(12) United States Patent
Murakami

(10) Patent No.: US 8,496,884 B2
(45) Date of Patent: Jul. 30, 2013

(54) STIRRING CONTAINER AND ANALYZER

(75) Inventor: Miyuki Murakami, Tokyo (JP)

(73) Assignee: Beckman Coulter, Inc., Brea, CA (US)

( * ) Notice: Subject to any disclaimer, the term of this patent is extended or adjusted under 35 U.S.C. 154(b) by 674 days.

(21) Appl. No.: 11/957,817

(22) Filed: Dec. 17, 2007

(65) Prior Publication Data

US 2008/0141784 A1 Jun. 19, 2008

Related U.S. Application Data

(63) Continuation of application No. PCT/JP2006/310920, filed on May 31, 2006.

(30) Foreign Application Priority Data

Jun. 17, 2005 (JP) ................................. 2005-178384
Oct. 19, 2005 (JP) ................................. 2005-304964

(51) Int. Cl.
  *G01F 1/20* (2006.01)
(52) U.S. Cl.
  USPC ...... 422/186.1; 422/50; 422/68.1; 422/82.05; 422/82.08; 422/82.09; 422/99; 422/102; 422/104; 422/939; 422/940; 422/401; 422/547; 422/549; 422/554; 366/108; 366/110; 366/111; 366/112; 366/114
(58) Field of Classification Search
  USPC ............ 366/108, 110, 111, 112, 114; 422/50, 422/68.1, 82.05, 82.08, 82.09, 99, 102, 104, 422/939, 940, 401, 547, 549, 554, 186.1
  See application file for complete search history.

(56) References Cited

U.S. PATENT DOCUMENTS

| 3,542,345 A | * | 11/1970 | Kuris ............................. 366/113 |
| 5,098,661 A | | 3/1992 | Froehlich et al. |
| 2002/0009015 A1 | * | 1/2002 | Laugharn et al. ............. 366/108 |
| 2004/0115097 A1 | | 6/2004 | Wixforth |
| 2004/0257906 A1 | | 12/2004 | Scriba et al. |
| 2005/0123457 A1 | * | 6/2005 | Tajima et al. ................. 422/130 |
| 2007/0253866 A1 | * | 11/2007 | Rousseau ........................ 422/64 |

FOREIGN PATENT DOCUMENTS

| DE | 1 032 5307 | 7/2004 |
| JP | 1-144846 | 10/1989 |

(Continued)

OTHER PUBLICATIONS

English-language abstract of Japanese Patent Publication No. 08-146007, published Jun. 7, 1996.

*Primary Examiner* — Brian R Gordon
*Assistant Examiner* — Shogo Sasaki
(74) *Attorney, Agent, or Firm* — Kilpatrick Townsend & Stockton LLP

(57) ABSTRACT

A stirring container in which liquid is contained is used in an analyzer for measuring a property of the liquid. The stirring container includes a recessed portion in which the liquid is held so that a meniscus is formed; and a sound wave generating unit disposed outside of a wall portion forming the recessed portion, and generates surface sound waves for stirring the liquid. The wall portion is configured so that a rising of the meniscus is lower than a rising of the meniscus formed by the liquid held in an assumed container whose cross section in a direction orthogonal to a depth direction of the recessed portion is the same as that of a circumscribed rectangle. The circumscribed rectangle is circumscribed about a portion, made of a same material as a part of the wall portion where the meniscus is formed, where the meniscus is formed in the relevant direction.

32 Claims, 15 Drawing Sheets

FOREIGN PATENT DOCUMENTS

| | | |
|---|---|---|
| JP | 3-69852 | 3/1991 |
| JP | 4-503566 | 6/1992 |
| JP | 3168886 | 3/2001 |
| JP | 2004-534633 | 11/2004 |
| JP | 2005-504623 | 2/2005 |
| WO | WO 2004/076046 A1 | 9/2004 |

* cited by examiner

US 8,496,884 B2

STIRRING CONTAINER AND ANALYZER

CROSS-REFERENCE TO RELATED APPLICATIONS

This application is a continuation of PCT international application Ser. PCT/JP2006/310920 filed May 31, 2006 which designates the United States, incorporated herein by reference, and which claims the benefit of priority from Japanese Patent Applications No. 2005-178384, filed Jun. 17, 2005, and No. 2005-304964, filed Oct. 19, 2005, incorporated herein by reference.

BACKGROUND OF THE INVENTION

1. Field of the Invention

The present invention relates to a stirring container which stirs a liquid held therein by sound wave contactlessly and to analyzer which uses this stirring container.

2. Description of the Related Art

Conventionally, an analyzer is known in which ultrasonic waves are radiated to a reaction container from the outside and a sound flow is generated in the liquid sample which the reaction container holds and the liquid sample is stirred and mixed contactlessly, in order to downsize a reaction container and avoid contamination of analytes (see German Patent No. 10325307 and Patent No. 3168886).

In recent years, calls for trace amount of sample and trace amount of reagent have been intensified, and further miniaturization of reaction containers for liquids of several µL order has been still more required. When the container volume is reduced in order to meet these requests, there are cases in which portions where the liquid stirring cannot be conducted occur. When a portion where the liquid stirring cannot be conducted occurs, the ratio of an actual sample to a reagent held in the container and the ratio of the sample and the reagent to cause chemical reactions differ significantly, and as a result, it becomes difficult to perform accurate analysis.

In addition, when ultrasonic waves of tens to hundreds of MHz or higher frequency are used to carry out contactless stirring for trace amount of liquid, the flow generated in the liquid is predominantly generated by sound flows. Consequently, when ultrasonic waves are used, sufficient stirring with the liquid of other portions cannot be expected once a stagnant portion where sound flow cannot penetrate is generated. When sufficient stirring cannot be conducted, for example, part of reagent remains unstirred with the analyte, and accurate measurement of the analyte cannot be conducted.

As described above, in a reaction container of analyzer that handles, particularly, liquids of tens to a few µL or less as objects to be stirred, it becomes important to suppress generation of this kind of stagnant portion or hold down the size of the stagnant portion generated.

SUMMARY OF THE INVENTION

A stirring container, in which liquid is contained, according to one aspect of the present invention is used in an analyzer for measuring a property of the liquid, and includes a recessed portion in which the liquid is held so that a meniscus is formed at a surface the liquid, the recessed portion being formed by a wall portion including side walls and a bottom wall; and a sound wave generating unit disposed outside of the wall portion, the sound wave generating unit generating surface sound waves for stirring the liquid held in the recessed portion. The wall portion is configured so that a rising of the meniscus formed by the liquid held in the recessed portion is lower than a rising of the meniscus formed by the liquid held in an assumed container whose cross section in a direction orthogonal to a depth direction of the recessed portion is the same as that of a circumscribed rectangle with a minimum area, the circumscribed rectangle being circumscribed about a portion where the meniscus is formed in the relevant direction, the portion where the meniscus is formed being made of a same material as a part of the wall portion where the meniscus is formed.

A stirring container, in which liquid is contained, according to another aspect of the present invention is used in an analyzer for measuring a property of the liquid, and includes a recessed portion in which the liquid is held so that a meniscus is formed at a surface the liquid, the recessed portion being formed by a wall portion including side walls and a bottom wall; and a sound wave generating unit disposed outside of the wall portion, the sound wave generating unit generating surface sound waves for stirring the liquid held in the recessed portion. A portion of the side walls in contact with the meniscus of the liquid has non-affinity for the liquid to define the meniscus.

A stirring container, in which liquid is contained, according to still another aspect of the present invention is used in an analyzer for measuring a property of the liquid, and includes a recessed portion in which the liquid is held so that a meniscus is formed at a surface the liquid, the recessed portion being formed by a wall portion including side walls and a bottom wall; and a sound wave generating unit disposed outside of the wall portion, the sound wave generating unit generating surface sound waves for stirring the liquid held in the recessed portion. An obtuse angle or a curved portion is formed between the adjacent side walls which form the recessed portion which comes into contact with the liquid in the direction of a flow of the liquid caused due to the surface sound waves.

An analyzer according to still another aspect of the present invention is for measuring a property of a liquid sample by stirring, using the stirring container in which the liquid sample is contained, the liquid sample containing an analyte and a reagent to allow them to react and to analyze the liquid sample.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 25:
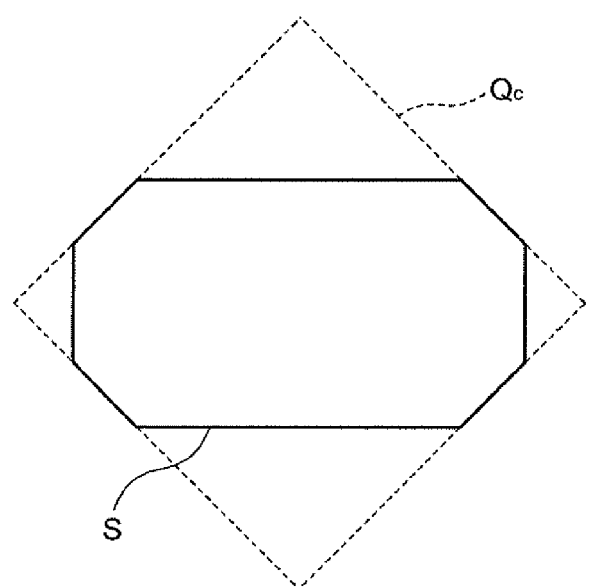
FIG. 25 is an explanatory diagram which explains the definition of a circumscribed rectangle which circumscribes the cross section of a recessed portion in the direction orthogonal to the depth direction at the portion where the meniscus is formed in the stirring container of the present invention.
Figure 26:
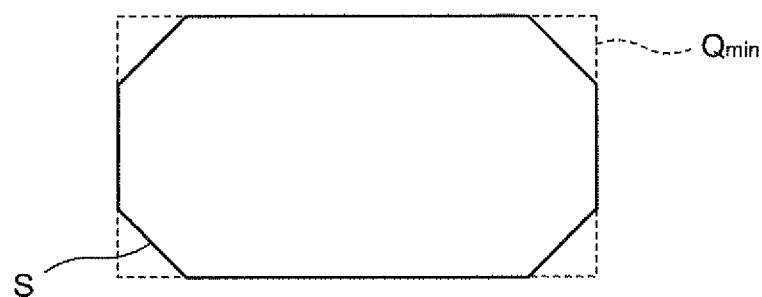
FIG. 26 is an explanatory diagram that explains the definition of a circumscribed rectangle of the minimum area of the circumscribed rectangles described in FIG. 25.

In the present description, a quadrangle which circumscribes the cross-sectional shape in the direction orthogonal to the depth direction of a concave portion in the portion where the meniscus is formed is, for example, when the cross-sectional shape in the horizontal direction of a concave portion Pc at the portion of a stirring container where the meniscus is formed is S, a quadrangle Qc and a quadrangle Qmin shown in dotted lines, as shown in FIG. 25 and FIG. 26. Consequently, a circumscribed rectangle of the minimum area should be the quadrangle Qmin in which the area shown in FIG. 26 is the minimum, of the quadrangles circumscribing the cross-sectional shape S.

Figure 27:
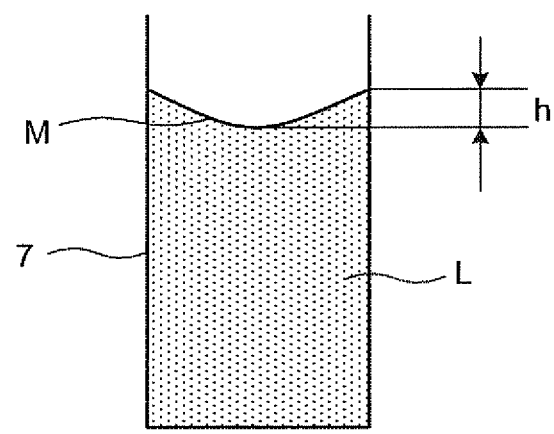
FIG. 27 is an explanatory diagram that explains the definition of the rising of the meniscus in the stirrer according to the present invention.

In addition, in the present description, the rising of the meniscus in a stirring container means the height from the lowest position of the meniscus in a liquid held to the top end of the meniscus, and for example, in a reaction container 7 shown in FIG. 27 discussed in the first embodiment, it means the height from the lowest position of the meniscus M of the liquid L to the top end of the meniscus M. Accordingly, it refers not only to the case shown in FIG. 27 in which the meniscus projects downwards but also to the case in which the meniscus projects upwards.

Figure 1:
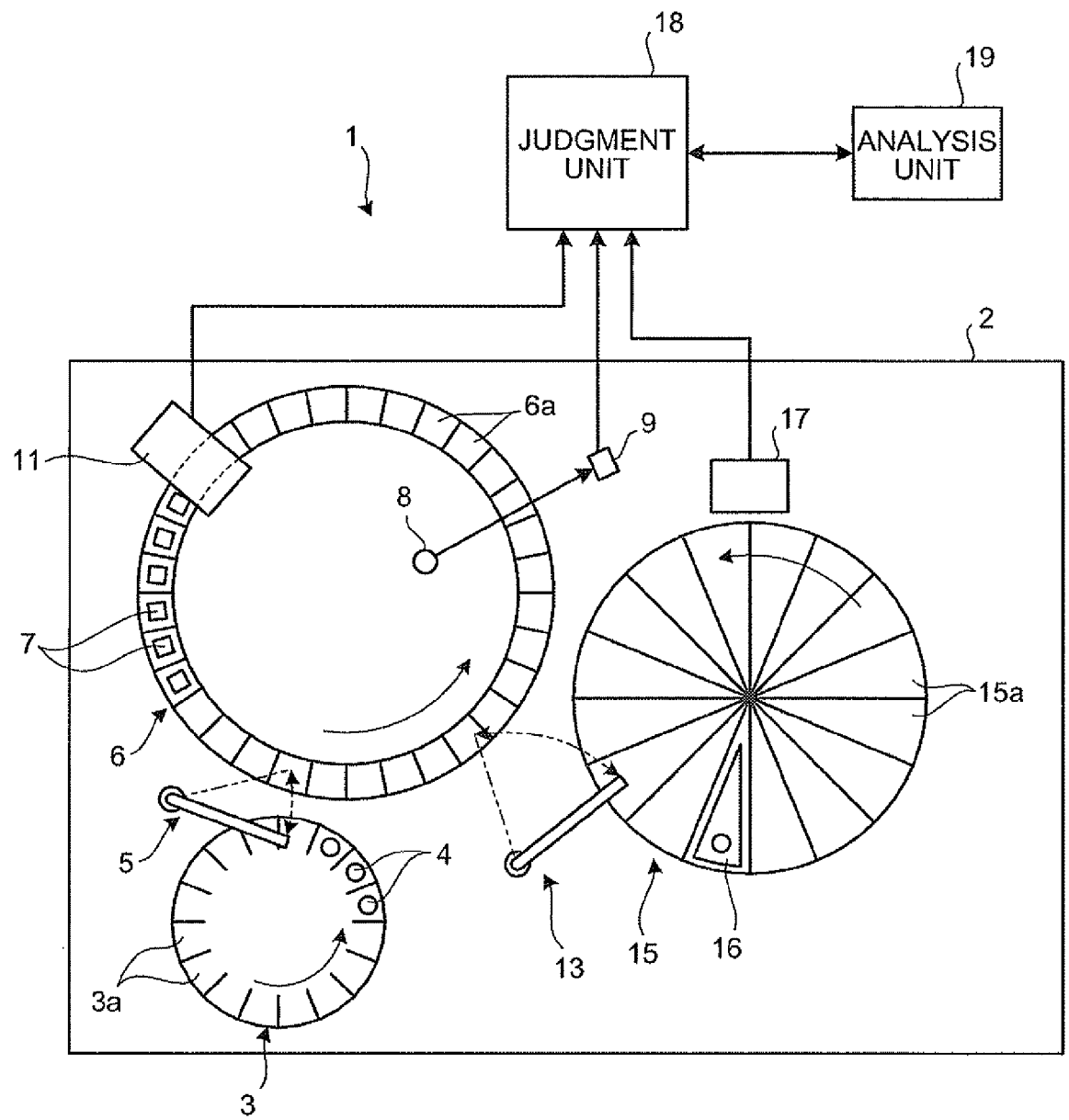
FIG. 1 is a schematic block diagram of an automatic analyzer showing a first embodiment of analyzer according to the present invention.
Figure 2:
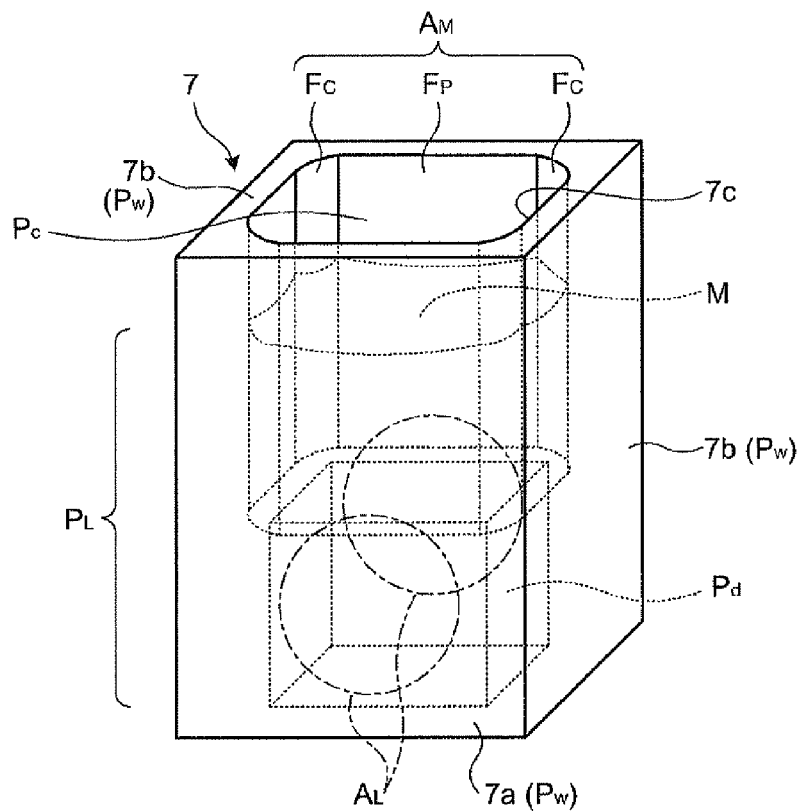
FIG. 2 is a perspective view that shows only a container of a reaction container used for the automatic analyzer of FIG. 1.
Figure 3:
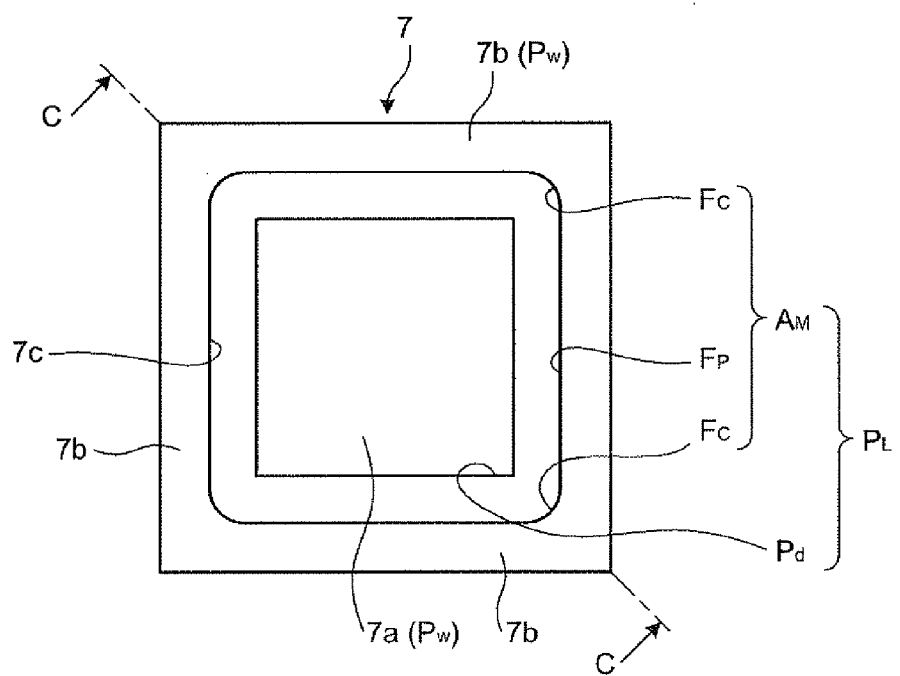
FIG. 3 is a plan view of the reaction container shown in FIG. 2.
Figure 4:
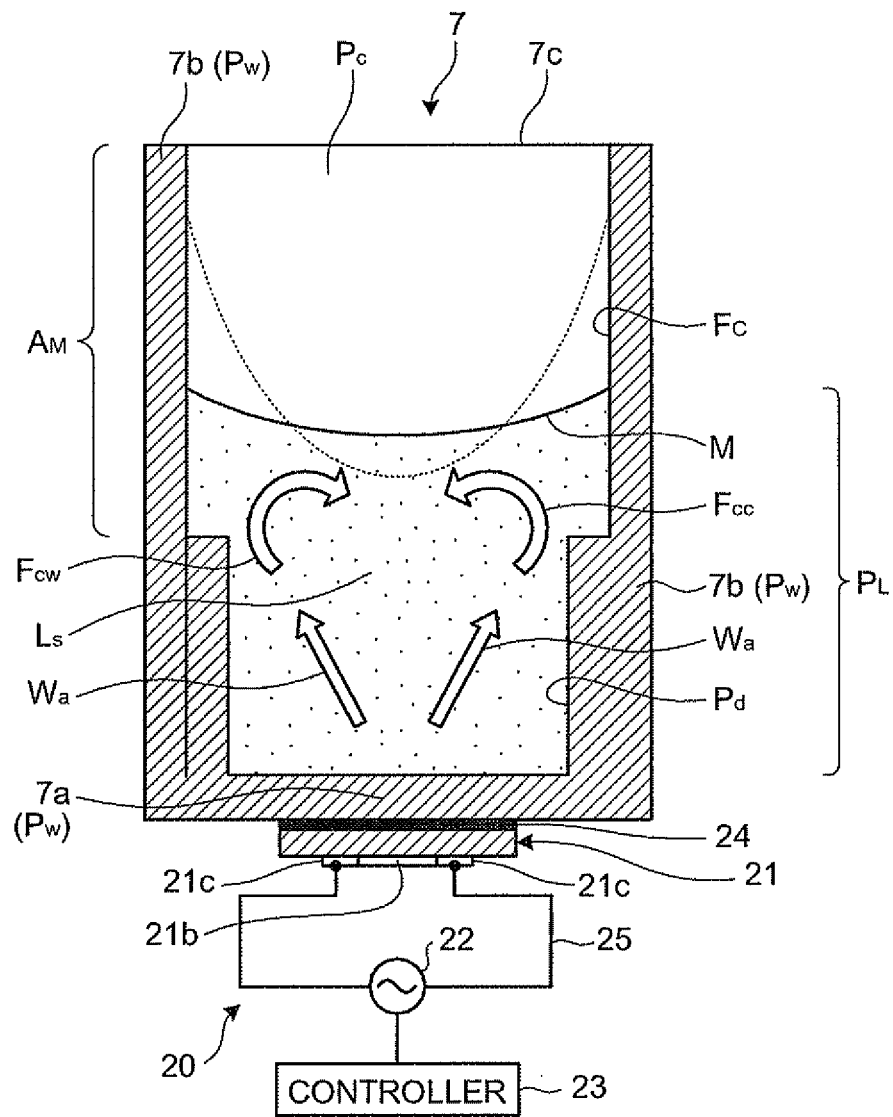
FIG. 4 is a schematic block diagram of the reaction container shown together with a stirrer and taken along line C-C of FIG. 3.

Referring to the figures, a first embodiment related to a stirring container of the present invention and analyzer using the stirring container is described. FIG. 1 is a schematic block diagram of automatic analyzer that shows the first embodiment of the analyzer according to the present invention. FIG. 2 is a perspective view that shows only the container of a reaction container used in the automatic analyzer of FIG. 1. FIG. 3 is a plan view of the reaction container shown in FIG. 2. FIG. 4 is a schematic block diagram that shows the reaction container taken along line C-C of FIG. 3, together with a stirrer.

As shown in FIG. 1, the automatic analyzer 1 is installed on a work bench 2 with a sample table 3, reaction table 6, and a reagent table 15 separated one another rotatably as well as positioning-free along the circumferential direction, respectively. In addition, the automatic analyzer 1 has a sample dispensing mechanism 5 installed between the sample table 3 and reaction table 6, and a reagent dispensing mechanism 13 is installed between the reaction table 6 and the reagent table 15.

The sample table 3 is rotated in the direction shown by an arrow by a drive unit (not illustrated) as shown in FIG. 1, and multiple storage chambers 3a disposed at regular intervals along the circumferential direction on the outer circumference are installed. Each storage chamber 3a houses removably a sample container 4 which houses the analyte.

The sample dispensing mechanism 5 is a means to dispense analyte into a reaction container 7 later discussed, and dispenses the analyte from multiple analyte containers 4 on the sample table 3 successively into the reaction container 7 later discussed.

The reaction table 6 is rotated in the direction shown by an arrow by a drive unit (not illustrated) different from that of the sample table 3 as shown in FIG. 1, and has multiple storage chambers 6a arranged at regular intervals along the circumferential direction on the outer circumference. Each storage chamber 6a has the reaction container 7 in which the analyte is allowed to react with the reagent as a stirring container removably housed. In addition, to the reaction table 6, a light source 8 and a discharger 11 are installed. The light source 8 radiates analysis light (340-800 nm) for analyzing a liquid sample in the reaction container 7 which is the reactant of the agent and the analyte. The optical beam for analysis radiated from the light source 8 penetrates the liquid sample in the reaction container 7 and is received by a light-receiving element 9 located at the position opposite to the light source 8. The light receiving element 9 is connected to the analysis unit 19 via the judgment unit 18. The analysis unit 19 analyzes the analyte composition, concentration, etc. of the analyte based on the absorbance of the liquid sample inside the reaction container 7. On the other hand, the discharger 11 is equipped with a discharge nozzle which is not illustrated, sucks the liquid sample after reaction from the reaction container 7 by the discharge nozzle, and discharges into a discharge container (not illustrated). Now, the reaction container 7 which has passed the discharger 11 is transferred to cleaning equipment not illustrated and cleaned, and then, again, is used for analysis of a new analyte.

The reagent dispensing mechanism 13 is a means for dispensing the reagent into the reaction container 7 and dispenses the reagent from the predetermined reagent container 16 of the reagent table 15 later discussed successively into reaction container 7.

The reagent table 15 is as shown in FIG. 1 rotated in the direction shown by the arrow by the drive unit not illustrated, and multiple storage chambers 15a formed in a fan-like form are installed. Each storage chamber 15a has a reagent container 16 removably housed. A plurality of reagent containers 16 are filled with predetermined reagents in accordance with inspection items, respectively and barcode labels (not illustrated) that indicate information concerning the reagent housed are affixed on the outside.

Now, on the outer circumferential portion of the reagent table 15, a reader 17 which reads the kind, lot, expiration date, and other information of the reagent recorded on the barcode label affixed to the reagent container 16 and outputs to a judgment unit 18 is installed. The judgment unit 18 is connected to the light receiving element 9, discharger 11, and reader 17, and for example, a microcomputer, etc. are used.

The automatic analyzer 1 configured as above allows the sample dispensing mechanism 5 to successively dispense analytes from multiple sample containers 4 of the sample table 3 into the reaction containers 7 conveyed along the circumferential direction by the rotating reaction table 6. The reaction containers 7 with analytes dispensed are conveyed to the vicinity of the reagent dispensing mechanism 13 by the reaction table 6, and from the predetermined reagent containers 16, reagents are dispensed. And while the reaction containers 7 with the reagents dispensed are being conveyed along the circumferential direction by the reaction table 6, the reagents and the analytes are stirred and reacted, and pass between the light source 8 and the light receiving element 9. In such an event, the liquid sample in the reaction container 7 is subject to photometry by the light receiving element 9, and the components, concentrations, etc. are analyzed by the analysis unit 19. And the reaction container 7 which has finished the analysis has the liquid sample after reaction discharged by the discharger 11, and is washed by a washing device not illustrated, and used for analysis of analytes again.

In such an event, the automatic analyzer 1 stirs by a stirrer the liquid sample inside the reaction container 7 conveyed along the circumferential direction by the reaction table 6 and allows the reagent to react with the analytes. The reaction container 7 used for stirring this liquid sample will be described as follows together with the stirrer.

The reaction container 7 transmits 80% or more of the light contained in the analysis light (340-800 nm) radiated from the light source 8 and the material with high affinity, for example, with high water affinity, for example, glass including heat-resistant glass is used. The reaction container 7 is equipped with a surface sound wave device 21, and as shown in FIG. 2, the outer shape of a horizontal cross section is formed into a quadrangle by the wall portion Pw including the bottom wall 7a and side wall 7b, and a recessed portion Pc which has an opening 7c for injecting the liquid is formed at the top in the vertical direction. The recessed portion Pc regulates and holds the liquid shape. In the reaction container 7, a liquid surface contact area AM to which a meniscus M that protrudes downwards is formed by a predetermined amount of liquid sample on the top of the inner surface of the liquid holding unit PL surrounded by the wall portion Pw. Now, in the present description, the liquid holding unit PL refers to the portion below the meniscus M of the recessed portion Pc which holds the liquid, and this applies to other embodiments, too.

In such an event, when a container is assumed, which has a cross-sectional shape in the horizontal direction same as the circumscribed quadrangle of the minimum area that circumscribes the cross-sectional shape in the horizontal direction in the liquid surface contact area AM where the meniscus M is formed and at the same time, is made up with the same material as the wall portion Pw of the liquid surface contact area AM were the meniscus is formed, the wall portion Pw is configured in such a manner that the rising of the meniscus M which the liquid held in the reaction container 7 forms is lower than the rising of the meniscus formed by the liquid held in the assumed container. That is, the side wall 7b consists of a curved surface FC in which the liquid contact area AM of the inner surface is bent in the horizontal direction and a vertical surface FP as shown in FIG. 2, and the adjacent vertical surfaces FP are connected by the curved surface FC. Consequently, the liquid surface contact area AM has the four corner portions with which the meniscus M of the liquid sample comes into contact being bent in the horizontal direction. Consequently, the side wall 7b has portions of varying wall thickness as shown in FIG. 2 and FIG. 3. In addition, the liquid holding unit PL has the bottom part of the liquid surface contact area AM formed into a recessed portion Pd of a rectangular parallelepiped by the bottom wall 7a and the side wall 7b. In this event, one set of side walls 7b parallel to each other have mutually opposed portions of the lower part of the liquid surface contact area AM shown by an alternate long and short dash line, which transmit the analytical optical beam radiated from the light source 8 and are used as the photometric unit AL that optically measures the liquid sample.

In addition, the reaction container 7 shall be of a protruded shape whose cross-section in the horizontal direction orthogonal to the depth direction of the recessed portion Pd in the liquid surface contact area AM where the meniscus is formed has an area smaller than the circumscribed rectangle Qmin shown in FIG. 26 and which contains all the segments that connect optional two points included in this horizontal cross section in this horizontal cross section so that the rising of the meniscus M which the liquid held forms becomes low. Furthermore, for the reaction container 7, the projected image of the opening 7c to the horizontal surface is formed in such a manner as to contain all the optional horizontal cross-sections of the liquid holding unit PL so that the cross-sectional area in the horizontal direction does not greatly vary in the vertical direction. In other words, the projected image of the recessed portion Pd to the horizontal surface includes all the cross-sections in the horizontal direction of the recessed portion Pd on the bottom wall 7a side from the meniscus M. Consequently, the liquid holding unit PL becomes a protruded shape which contains all segments that connect optional two points inside the liquid holding unit PL in the liquid holding unit PL.

In addition, the photometric unit AL is set in such a manner that the cross-sectional area in the horizontal direction is smaller than the cross-sectional area in the horizontal direction inside the liquid surface contact area AM. And the liquid surface contact area AM is set in such a manner that the curvature of the curved surface FC that is bent in the horizontal direction is smaller than the curvature in the cross-section in the horizontal direction of the photometric unit AL. Consequently, because the liquid surface contact area AM has the four corner portions with which the meniscus M of the liquid sample comes into contact bent in the horizontal direction as compared to a conventional reaction container (corresponding to an assumed container which has the circumscribed rectangle Qmin whose area is the minimum) to which the side wall 7b comes into contact at 90°, the steep rising of the meniscus M in this curved surface FC can be suppressed.

The stirrer 20 is disposed in the lower part of the storage chamber 6a between the light source 8 and light receiving element 9 disposed opposite to each other to the position where the reagent dispensing mechanism 13 dispenses the reagent to the reaction container 7 and as shown in FIG. 4, has the power supply 22, controller 23, and acoustic matching layer 24 and stirs the liquid which the reaction container 7 holds by driving the surface sound wave device 21.

Figure 5:
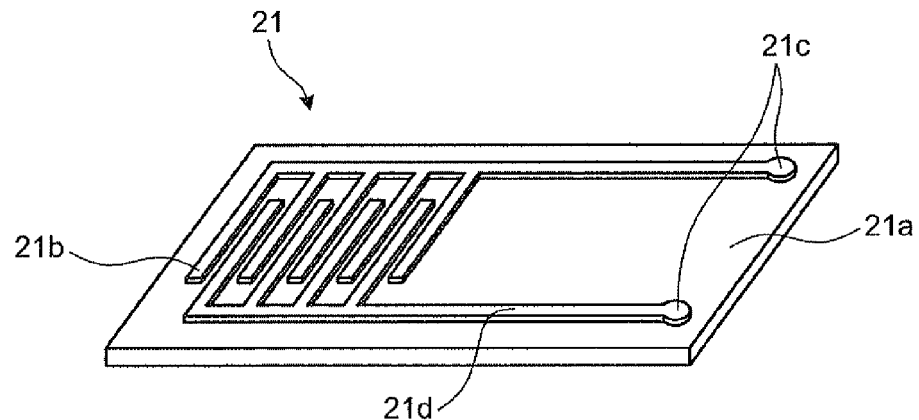
FIG. 5 is a perspective view that shows a sound wave generating unit which the reaction container related to the first embodiment has.
Figure 6:
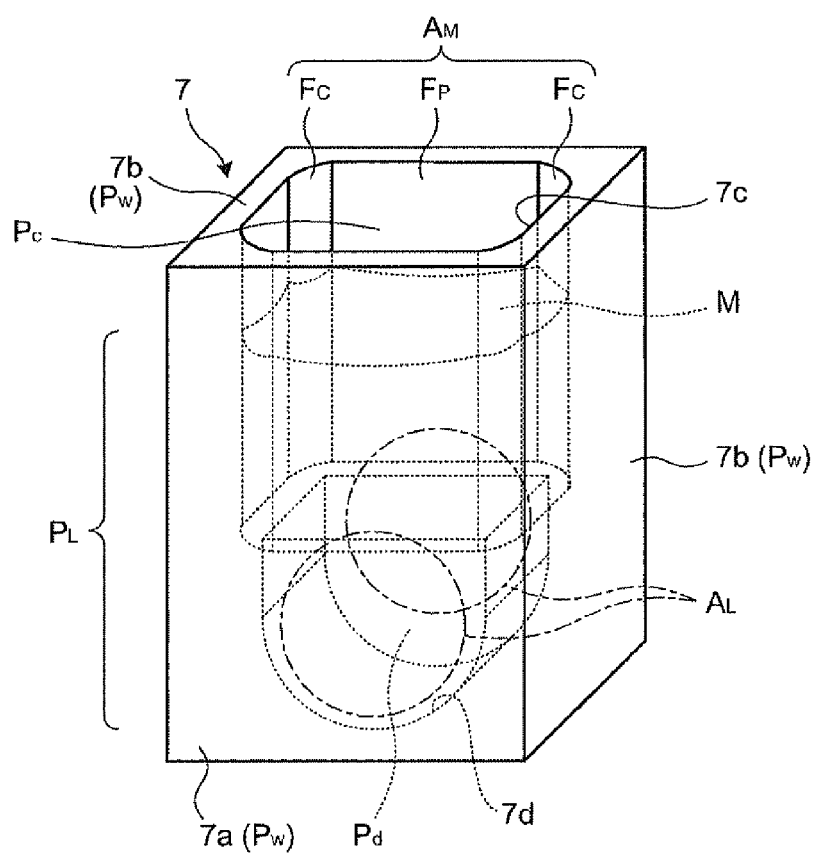
FIG. 6 is a perspective view that shows a first modification of the reaction container related to the first embodiment.

The surface sound wave device 21 is a sound wave generating unit that generates ultrasonic waves which are surface sound waves, and as shown in FIG. 4 and FIG. 5, has an oscillator 21b composed with a gold or other interdigital transducer (IDT) installed on the surface of lithium niobate or other piezoelectric substrate 21a. The oscillator 21b converts the electric power sent from the power supply 22 into the surface sound wave (sound wave) and as shown in FIG. 4, is installed to the bottom surface of the bottom wall 7a via the acoustic matching layer 24. In such an event, the surface sound wave device 21 has the wavelength in the liquid held in the reaction container 7 of the sound wave which the oscillator 21b generates practically sufficiently short with respect to the rising h of the meniscus which the liquid L forms in the reaction container 7 shown in FIG. 27. That is, the rising h of the meniscus which the liquid L held by the reaction container 7 forms is $h \geqq 10 \cdot \lambda_L$ when $\lambda_L$ denotes the wavelength of the sound wave in the liquid L. In addition, the oscillator 21b is connected across an electric terminal 21c by a conductor circuit 21d as shown in FIG. 5. Because the surface sound wave device 21 uses the interdigital transducer (IDT) as the oscillator 21b, a compact configuration with simple construction can be achieved.

The power supply 22 is connected across the electric terminal 21c by wiring 25 as shown in FIG. 4 and supplies several MHz to hundreds of MHz high-frequency alternate current to the surface acoustic sound device 21. The controller 23 controls properties (frequency, intensity, phase, wave properties) of the sound wave which the surface acoustic sound device 21 generates, waveform (sinusoidal wave, triangular wave, rectangular wave, burst wave, etc.) or modulation (amplitude modulation and frequency modulation), etc by controlling the power source 22. The acoustic matching layer 24 is a means to optimize the acoustic impedance between the reaction container 7 and the surface sound wave device 21, and gel, liquid, etc. can be used in addition to epoxy resin and other adhesives, shellac, and others. The acoustic matching layer 24 is adjusted to have the thickness of $n \cdot \lambda/4$ (n: odd number) with respect to the wavelength $\lambda$ of the frequency which the surface sound wave device 21 generates in order to increase the sound wave transmission efficiency. Or the acoustic matching layer 24 shall be adjusted to be as thin as possible.

Consequently, the reaction container 7 has the retained liquid sample stirred as follows by the stirrer 20. First of all, the stirrer 20 drives the surface sound wave device 21 by the electric power supplied from the power supply 22 under the control by the controller 23. By this, the surface sound wave device 21 causes the oscillator 21b shown in FIG. 5 to induce sound wave. The induced sound wave propagates to the bottom wall 7a of the reaction container 7 through the inside of the piezoelectric substrate 21a and the acoustic matching layer 24, and as shown in FIG. 4, the sound wave Wa shown by an arrow leaks from the inner surface of the bottom wall 7a to obliquely upward and into the liquid sample Ls which has close acoustic impedance.

As a result, in the liquid sample Ls, as shown in FIG. 4, counterclockwise sound flow Fcc and clockwise sound flow Fcw which reach the meniscus M are generated by the sound wave Wa, and sound flows Fcc and Fcw are dominant for the flow in the liquid sample Ls. In such an event, the reaction container 7 has the curved surface FC and vertical surface FP in which the liquid surface contact area AM of the inner surface is bent in the horizontal direction in the meniscus M and the curvature FC and vertical surface FP come into contact alternately. Consequently, the liquid sample Ls has the steep rising of the meniscus M in contact at the curvature FC portion suppressed as shown in FIG. 4 and becomes close to flatness as shown by the solid line. In this event, in FIG. 4, the broken line shows the meniscus M in the conventional reaction container and this same principle shall be applied to the following description, too.

Consequently, because as shown in FIG. 4, the meniscus M becomes nearly flat at the portion in contact with the curvature FC, sound flows Fcc and Fcw easily enter the portion where the liquid surface contact area AM comes into contact with the meniscus M by the sound flows Fcc and Fcw. As a result, the automatic analyzer 1 using the reaction container 7 and the stirrer 20 is able to uniformly stir the liquid sample Ls contactlessly over a wide range from the bottom unit to the meniscus M. In addition, because the reaction container 7 is used housed in the storage chamber 6a installed to the reaction table 6, it can be used in a conventional automatic analyzer as it is.

In this event, by coating or sputtering water-repellent treatment agent such as fluororesin, etc. to the liquid surface area AM with which a predetermined amount of liquid sample comes into contact, the reaction container 7 may be provided with water-repellent treatment. Providing this kind of water-repellent treatment, the reaction container 7 has the meniscus M of the held liquid sample protruding upward. As a result, the reaction container 7 has the sound flows Fcc and Fcw easily entering the portion where the liquid surface contact area AM and the meniscus M that protrudes upwards come into contact with each other, and stirring by the stirrer 20 can be uniformly performed. Treatment provided for the liquid contact area AM should have the non-affinity for the liquid which the reaction container 7 holds, and shall not be limited to the water-repellent treatment only.

Figure 7:
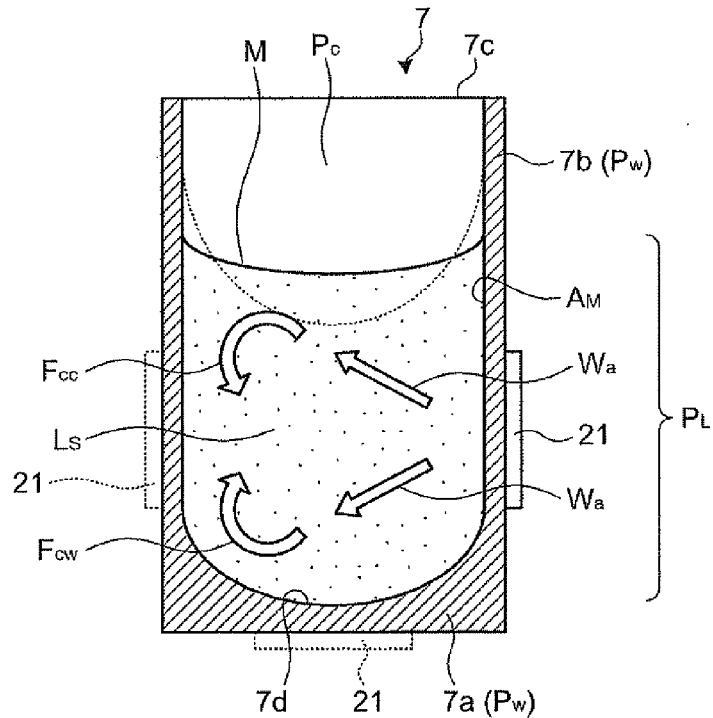
FIG. 7 is a longitudinal cross-sectional view that shows a second modification of the reaction container related to the first embodiment.

In addition, the reaction container 7 may have the inner bottom surface 7d of the recessed portion Pd formed at the bottom part of the liquid contact area AM bent to a shape corresponding to the cross-sectional form of the optical beam for analysis that penetrates the photometric unit AL. By doing this, the reaction container 7 can improve the stirring efficiency without generating the stagnant portion while securing the photometric accuracy, because the clockwise acoustic flow Fcw generated on the down side smoothly flows along the curve of the inner bottom surface 7d, of the two-directional sound flows Fcc and Fcw generated by the sound wave Wa radiated from the surface sound wave device 21 mounted to the outer surface of the side wall 7b as shown in FIG. 7. In such an event, the reaction container 7 may have the surface sound wave device 21 installed to the outer surface (see the dotted line) of the side wall 7b opposite to the side wall 7b or to the outer surface (see the dotted line) of the bottom wall 7a.

In addition, the reaction container 7 has portions of varying wall thickness at the bottom wall 7a in addition to the side wall 7b.

Figure 8:
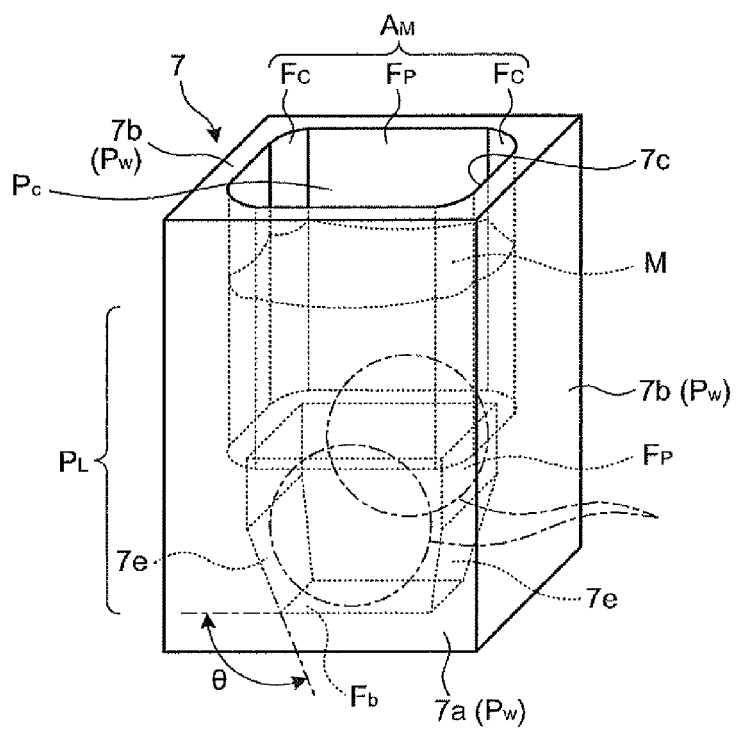
FIG. 8 is a perspective view that shows a third modification of the reaction container related to the first embodiment.
Figure 9:
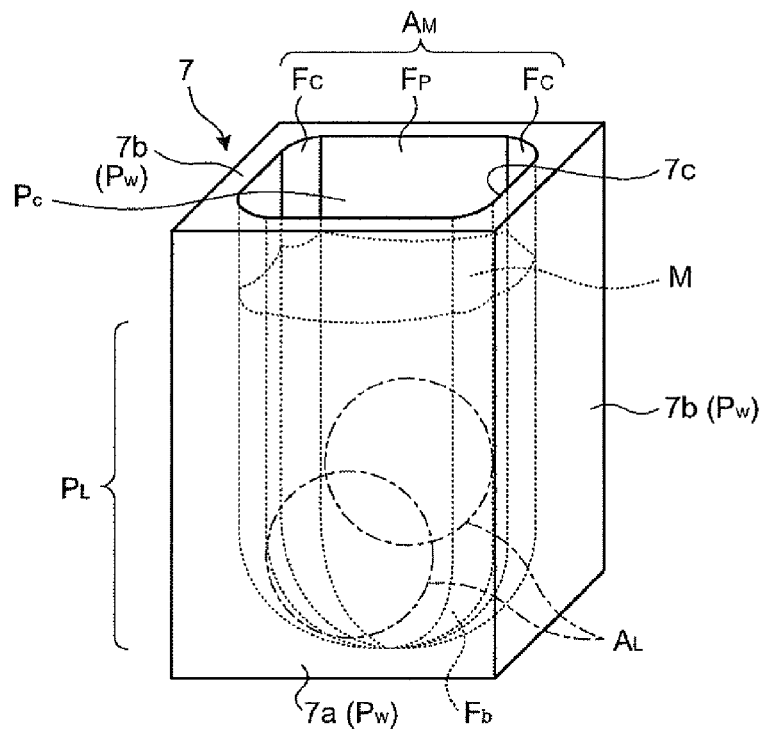
FIG. 9 is a perspective view that shows a fourth modification of the reaction container related to the first embodiment.

Furthermore, the reaction container 7 may have an inclined plane 7e which comes into contact with the inner bottom surface Fb of the recessed portion Pd at an obtuse angle θ on the side wall 7b inner surface adjacent to the side wall 7b where the photometric unit Al is formed as shown in FIG. 8. By doing this, the reaction container 7 can improve the stirring efficiency because the sound flow is guided along the inclined plane 7e. Furthermore, as is the case of the reaction container 7 shown in FIG. 9, extending each curved surface FC and each vertical surface FP that compose the liquid surface contact area AM downwards and at the same time, making the inner bottom surface Fb into a curved surface that consists of nearly same sphere as the radius of the cross section of optical beam for analysis that penetrates the photometric unit AL can result in the same effects. Consequently, as is the case of the reaction container 28 shown in FIG. 10, the liquid surface contact area AM may be configured by a vertical surface FP and a curved surface FBC which is larger than the curved surface FC of the reaction container 7. In such an event, the reaction container 28 is formed on a curved surface in which the inner bottom surface Fb is protruded downwards towards the opposite side wall 28c from the side wall 28c side adjacent to the side wall 28b on which the photometric unit AL is formed.

Figure 11:
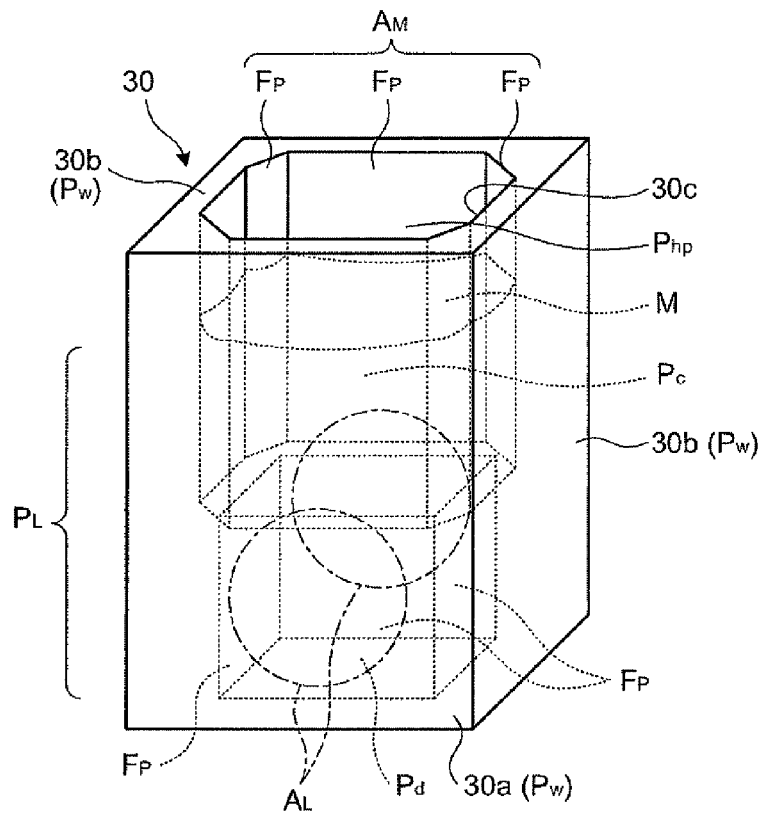
FIG. 11 is a perspective view that shows a reaction container related to the second embodiment with a surface sound wave device removed.
Figure 12:
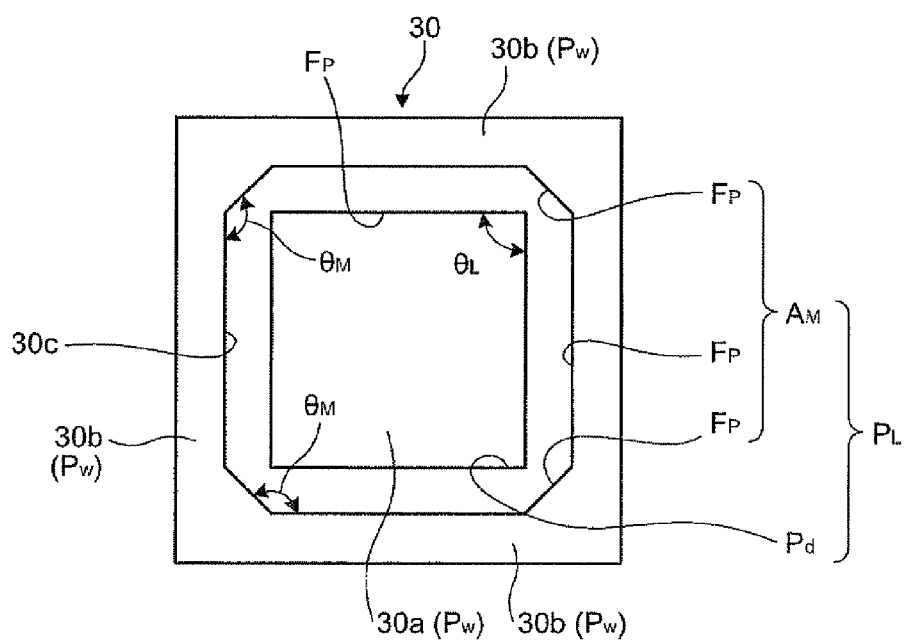
FIG. 12 is a plan view of the reaction container shown in FIG. 11.
Figure 13:
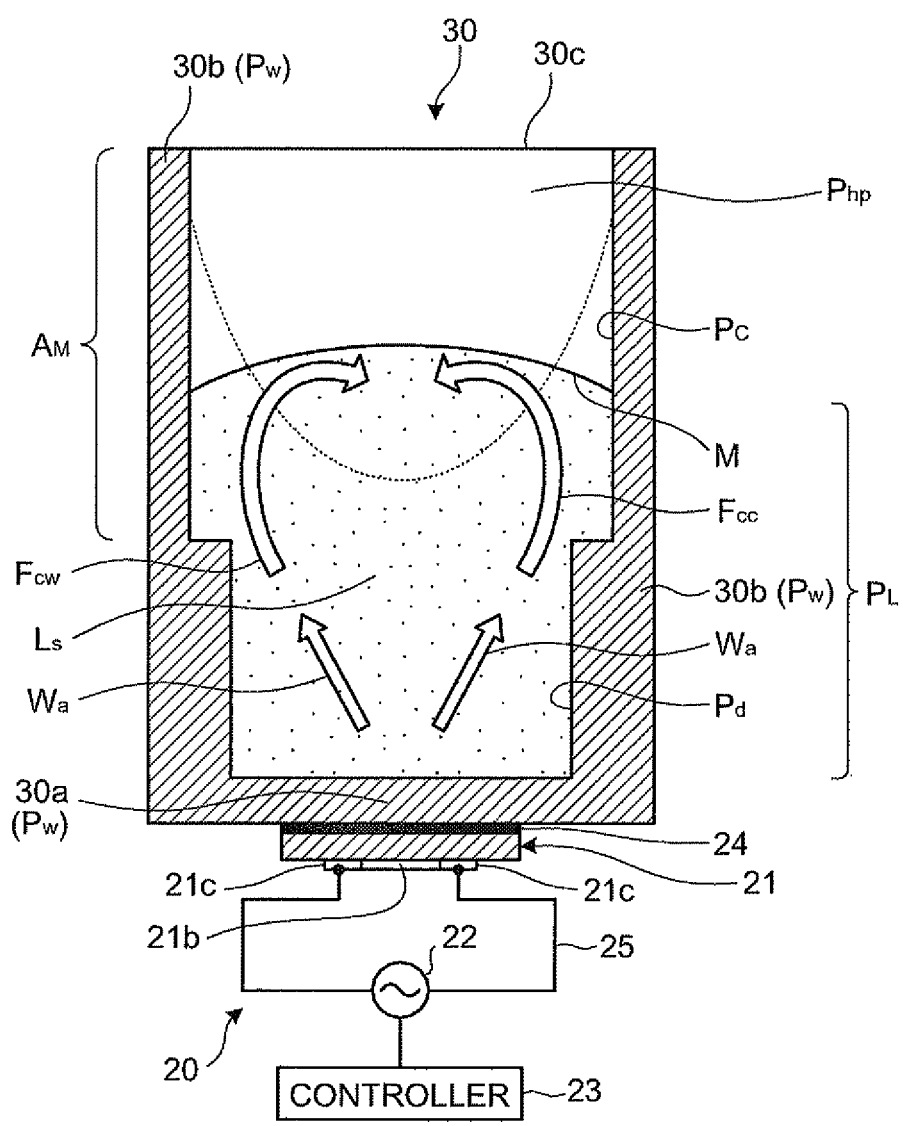
FIG. 13 is a longitudinal cross-sectional view that shows a reaction container related to a second embodiment which has the reaction container and the surface sound wave device.

Next, referring to drawings, a second embodiment of the present invention will be described in detail. The reaction container of the first embodiment has a curved surface in which the liquid surface contact area is bent in the horizontal direction and a vertical surface, whereas the reaction container of the second embodiment has the liquid contact area composed with the vertical surfaces with which planes adjacent in the horizontal direction come into contact at an obtuse angle. In each of the embodiments described in the following, the automatic analyzer 1 same as that of the first embodiment is used and the same reference numerals are assigned for the same members whose configuration is same as that of the first embodiment. Consequently, the reaction container is discussed as follows. FIG. 11 is a perspective view that shows a reaction container related to the second embodiment with the surface sound wave device 2 removed. FIG. 12 is a plan view of the reaction container shown in FIG. 11. FIG. 13 is a longitudinal cross-sectional view that shows the reaction container of the present invention which has a reaction container and a surface sound wave device.

For the reaction container 30, same as the reaction container 7, material that transmits 80% or more of the light included in the analysis light (340-800 nm) radiated from the light source 8, for example, glass including heat-resistant glass, is used. The reaction container 30 is used housed in the storage chamber 6a installed to the reaction table 6. The reaction container 30 is equipped with the surface sound wave device 21, and as shown in FIG. 11, has the outer shape of the horizontal cross section formed into a quadrangle by the wall portion Pw including bottom wall 30a and side wall 30b, and has a recessed portion Pc which has an opening 30c for liquid injection at the top formed in the vertical direction. The recessed portion Pc regulates and holds the liquid shape. The reaction container 30 has the liquid surface contact area AM in contact with the meniscus M protruded downwards formed by a predetermined amount of liquid sample at the inner top part of the liquid holding unit PL surrounded by the wall portion Pw. The liquid surface contact area AM has a hydrophobic unit Php with water-repellent treatment provided by coating or sputtering a water-repellent agent such as fluororesin, etc. to the surface formed as shown in FIG. 11.

Furthermore, in the reaction container 30, vertical surfaces FP to which the inner-surface liquid surface contact areas AM is adjacent in the horizontal direction come into contact at an obtuse angle θM. Consequently, the side wall 30b has portions with varying wall thickness as shown in FIG. 11 and FIG. 12. Furthermore, the liquid holding unit PL has the lower part of the liquid surface contact area AM formed into a recessed portion Pd of a rectangular parallelepiped shape by the inner surface of the bottom wall 30a and the vertical surface FP of the side wall 30b. In this event, one set of side walls 30b parallel to each other have mutually opposed portions of the lower part of the liquid surface contact area AM shown by an alternate long and short dash line, which transmit the optical beam for analysis radiated from the light source 8 and are used as the photometric unit AL that optically measures the liquid sample.

In such an event, for the reaction container 30, the projected image of the opening 30c to the horizontal surface is formed in such a manner as to contain all the optional horizontal cross-sections of the liquid holding unit PL so that the cross-sectional area in the horizontal direction does not greatly vary in the vertical direction. In other words, the projected image of the recessed portion Pd to the horizontal surface includes all the cross-sections in the horizontal direction of the recessed portion Pd on the bottom wall 30a side from the meniscus M. Consequently, the liquid holding unit PL becomes a protruded shape which contains all segments that connect optional two points inside the liquid holding unit PL in the liquid holding unit PL. In other words, in the recessed portion Pd, the space in which the portion of the bottom wall 30a side from the portion where the meniscus M is formed occupies becomes a protruded shape that includes all segments that connect optional two points included in a space. In addition, the photometric unit AL is set in such a manner that the cross-sectional area in the horizontal direction becomes smaller than the cross sectional area in the horizontal direction in the liquid surface contact area AM.

And in the liquid contact area AM, the angle θM at which vertical surfaces FP adjacent in the horizontal direction come into contact is set to be larger than the angle θL (=90°) at which vertical surfaces FP adjacent in the horizontal direction of the photometric unit AL (θM>θL). Consequently, at four corner portions where the meniscus M of the liquid sample comes into contact, the vertical surfaces FP adjacent in the horizontal direction come into contact at an obtuse angle as compared to conventional reaction container in which the side wall 30b comes into contact at 90°, and the meniscus M of the liquid sample becomes an upward protruded shape as shown in FIG. 13 by the hydrophobic unit Php.

The reaction container 30 configured as above drives the surface sound wave device 21 mounted to the outer surface of the bottom wall 30a via the acoustic matching layer 24 by the stirrer 20 as shown in FIG. 13, and the liquid sample held in the liquid holding unit PL is stirred as follows. First of all, the stirrer 20 drives the surface sound wave device 21 by the electric power supplied from the power supply 22 under the control by the controller 23. By this, the surface sound wave device 21 causes the oscillator 21b shown in FIG. 5 to induce sound wave. The induced sound wave propagates to the bottom wall 30a of the reaction container 30 through the acoustic matching layer 24, and as shown in FIG. 13, the sound wave Wa shown by an arrow leaks from the inner surface of the bottom wall 30a to obliquely upward and into the liquid sample Ls which has close acoustic impedance.

As a result, in the liquid sample Ls, counterclockwise sound flow Fcc and clockwise sound flow Fcw which reach the meniscus M are generated by the sound wave Wa. In such an event, the reaction container 30 has the meniscus M of the liquid sample held in the upward protruded shape because the hydrophobic unit Php is formed on the surface of the liquid surface contact area AM. As a result, the reaction container 30 has the sound flows Fcc and Fcw more easily entering the portion where the liquid surface contact area AM and the meniscus M that protrudes upwards come into contact with each other than the case in which the planes of the liquid contact area AM which are adjacent in the horizontal direction are made into vertical surfaces FP which come into contact at an angle δM, an obtuse angle, and stirring by the stirrer 20 can be uniformly performed. In such an event, sound flows Fcc and Fcw are predominant for the flow in the liquid sample Ls. Consequently, the automatic analyzer 1 using the reaction container 30 is able to uniformly stir the liquid sample Ls contactlessly over a wide range from the bottom unit to the meniscus M by these two sound flows Fcc and Fcw. In addition, because the reaction container 30 is used housed in the storage chamber 6a installed to the reaction table 6, it can be used in a conventional automatic analyzer as it is.

In such an event, the surface sound wave device 21 used in the embodiments described below has the wavelength in the liquid sample Ls held in the reaction container 30 of the sound wave which the oscillator 21b generates practically sufficiently short with respect to the rising of the meniscus M which the liquid Ls forms in the reaction container 30. It is same as in the case of the first embodiment in that the rising h of the meniscus M is $h \geq 10 \cdot \lambda_L$ when $\lambda_L$ denotes the wavelength of the sound wave in the liquid Ls.

Figure 14:
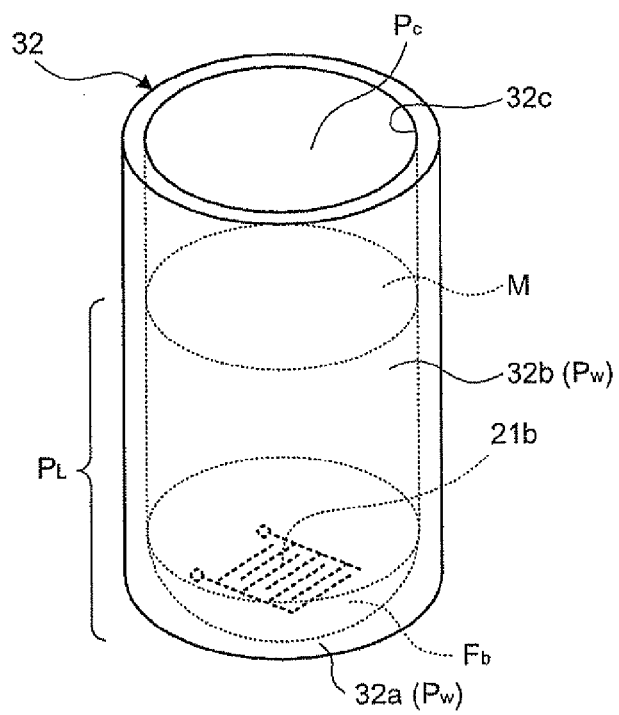
FIG. 14 is a perspective view that shows a reaction container related to a third embodiment with the surface sound wave device removed.
Figure 15:
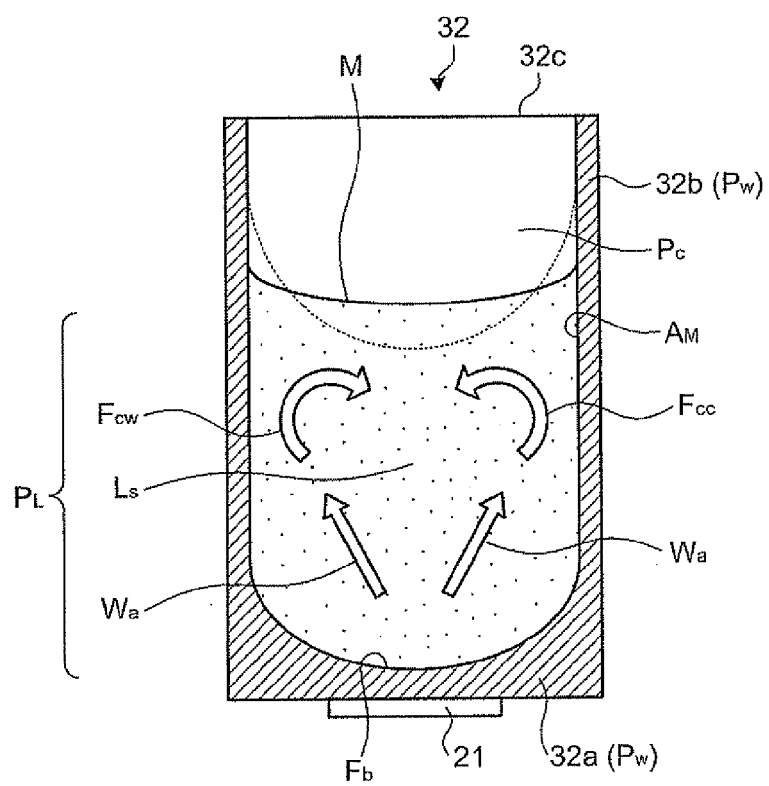
FIG. 15 is a longitudinal cross-sectional view that shows a reaction container according to the present invention with the surface sound wave device installed.

Referring now to FIG. 14 and FIG. 15, a stirring container related to the third embodiment of the present invention will be described in detail. The reaction container of the first embodiment has a curved surface in which the liquid surface contact area is bent in the horizontal direction and a vertical surface, whereas the reaction container of the third embodiment has a curved surface in which the liquid surface contact area is bent in the horizontal direction. FIG. 14 is a perspective view that shows the reaction container related to the third embodiment with the surface sound wave device removed. FIG. 15 is a longitudinal cross-sectional view that shows the reaction container of the present invention with the surface acoustic device installed.

The reaction container 32 is equipped with the surface sound wave device 21, and as shown in FIG. 14, the outer shape of the horizontal cross section is formed into a circular form by the wall portion Pw that contains the bottom wall 32a and the side wall 32b, and a recessed portion Pc which has an opening 32c for liquid injection is formed at the top in the vertical direction. The recessed portion Pc regulates and holds the liquid shape. The reaction container 32 has the liquid surface contact area AM to which the meniscus M protruded downwards by a predetermined amount of the liquid sample formed at the top of the inner surface of the liquid holding unit PL surrounded by the wall portion Pw. The bottom wall 32a has the center of the inner bottom surface Fb indented downwards convexly in a spherical shape as shown in FIG. 14 and FIG. 15. Consequently, in the bottom wall 32a, portions with varying wall thickness exist. In addition, in the bottom wall 32, the surface sound wave device 21 is mounted to the flat portion on the outside (see FIG. 15). On the other hand, the side wall 32b is composed with the curved surface in which the liquid surface contact area AM on the inner surface is bent in the horizontal direction, as shown in FIG. 14.

In such an event, when a container is assumed, which has a cross-sectional shape in the horizontal direction same as the circumscribed quadrangle Qmin (see FIG. 26) of the minimum area that circumscribes the cross-sectional shape in the horizontal direction where the meniscus M is formed and at the same time, is made up with the same material as the wall portion Pw of the portion where the meniscus is formed, the wall portion Pw is configured in such a manner that the rising of the meniscus M which the liquid held in the reaction container 7 is lower than the rising of the meniscus formed by the liquid held in the assumed container. That is, the side wall 32b consists of a curved surface in which the liquid contact area AM of the inner surface is bent in the horizontal direction as shown in FIG. 14. Consequently, the liquid surface contact area AM has the portions with which the meniscus M of the liquid sample comes into contact being bent in the horizontal direction, and therefore, as compared to the conventional reaction container of a quadratic prism where the side wall comes into contact at 90°, the steep rising of meniscus M of the liquid sample can be suppressed as shown in FIG. 15.

In addition, the reaction container 32 shall be of a protruded shape whose cross-section in the horizontal direction orthogonal to the depth direction of the recessed portion Pd in the liquid surface contact area AM where the meniscus is formed has an area smaller than the circumscribed rectangle Qmin shown in FIG. 26 and which contains all the segments that connect optional two points included in this horizontal cross section in this horizontal cross section so that the rising of the meniscus M which the liquid held forms becomes low. In other words, the recessed portion Pc has a space which the bottom wall 32a side portion occupies rather than the portion in which the meniscus M is formed becomes a protruded shape which contains all segments that connect optional two points inside the liquid holding unit PL in the liquid holding unit PL. Furthermore, for the reaction container 7, the projected image of the opening 7c to the horizontal surface is formed in such a manner as to contain all the optional horizontal cross-sections of the liquid holding unit PL so that the cross-sectional area in the horizontal direction does not greatly vary in the vertical direction. In other words, the projected image of the recessed portion Pd to the horizontal surface includes all the cross-sections in the horizontal direction of the recessed portion Pd on the bottom wall 32a side from the meniscus M. Consequently, the liquid holding unit PL becomes a protruded shape which contains all segments that connect optional two points inside the liquid holding unit PL in the liquid holding unit PL.

Consequently, when the reaction container 32 causes the surface sound wave device 21 to be driven by the stirrer 20, the sound wave induced by the oscillator 21b propagates to the bottom wall 32a of the reaction container 32 through the inside of the piezoelectric substrate 21a and the acoustic matching layer 24, and as shown in FIG. 15, the sound wave Wa shown by an arrow leaks from the inner bottom surface Fb of the bottom wall 32a to obliquely upward and into the liquid sample Ls which has close acoustic impedance.

As a result, in the liquid sample Ls, as shown in FIG. 15, counterclockwise sound flow Fcc and clockwise sound flow Fcw which reach the meniscus M are generated by the sound wave Wa, and sound flows Fcc and Fcw are predominant for the flow in the liquid sample Ls. In such an event, the reaction container 32 has the steep rising of the meniscus M in the liquid surface contact area AM suppressed as shown in FIG. 15 as is the case of the reaction container 7 shown in FIG. 2 and FIG. 4, and becomes close to flatness as shown by the solid line. The bottom wall 32a has the center of the inner bottom surface Fb indented downwards convexly in a spherical shape.

Consequently, as shown in FIG. 15, the automatic analyzer 1 using the reaction container 32 and the stirrer 20 uniformly stir the liquid sample Ls contactlessly over a wide range from the bottom unit to the meniscus M without forming any stagnant portion because the two sound flows Fcc and Fcw are easy to enter the portion where the liquid surface contact area AM comes into contact with the meniscus M and at the same time, sound flows Fcc and Fcw flow more smoothly than the conventional reaction container whose inner bottom surface is flat. In addition, because the reaction container 32 is used housed in the storage chamber 6a installed to the reaction table 6, it can be disposed to the storage chamber that houses a cuvette of conventional automatic analyzer and can be used as it is.

Figure 16:
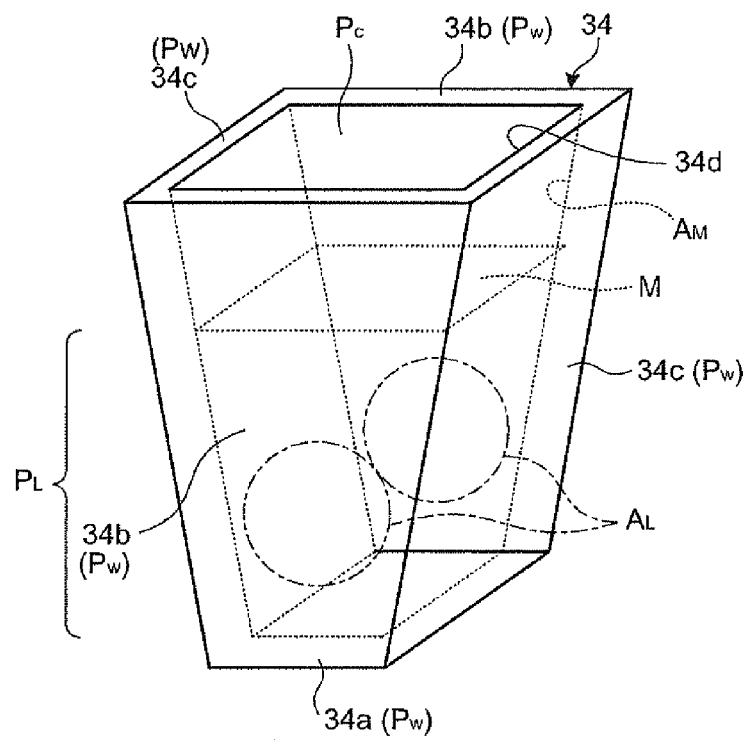
FIG. 16 is a perspective view that shows only the container of the reaction container related to a fourth embodiment.
Figure 17:
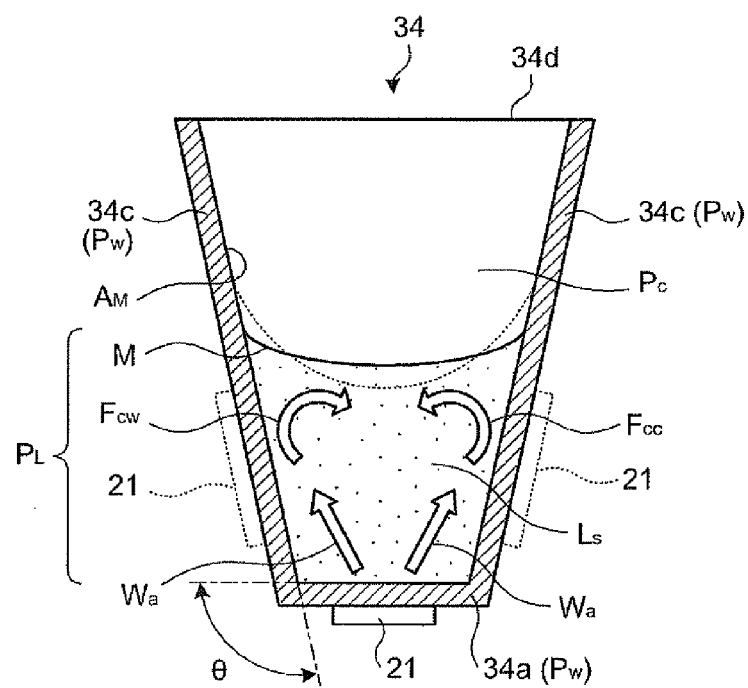
FIG. 17 is a longitudinal cross-sectional view of a reaction container according to the present invention which has the reaction container and the surface sound wave device.

Referring now to FIG. 16 and FIG. 17, a reaction container related to a fourth embodiment of the present invention will be described in detail. The reaction container of the first embodiment has a curved surface in which the liquid surface contact area is bent in the horizontal direction and a vertical surface, whereas the reaction container of the fourth embodiment has one set of opening side walls in which the liquid contact area opens outwards to upwards. FIG. 16 is a perspective view that shows only the container of the reaction container related to the fourth embodiment. FIG. 17 is a longitudinal cross-sectional view that shows a reaction container and the reaction container of the present invention which has a surface sound wave device.

The reaction container 34 is formed by the material same as that of the reaction container 7, and is used housed in the storage chamber 6a installed to the reaction table 6. The reaction container 34 is equipped with the surface sound wave device 21, and as shown in FIG. 16, has the outer shape of a horizontal cross section formed into a quadrangle by the bottom wall 34a, one set of mutually parallel side walls 34b, and the wall portion Pw including at least one set of opening side walls 34c adjacent to the parallel side wall 34b, and has a recessed portion Pc which has an opening 34d for injecting the liquid formed at the top in the vertical direction. The recessed portion Pc regulates and holds the liquid shape. In the reaction container 34, a liquid surface contact area AM to which a meniscus M that protrudes downwards is formed by a predetermined amount of liquid sample on the top of the inner surface of the liquid holding unit PL surrounded by the wall portion Pw.

The bottom wall 34a has the surface sound wave device 21 mounted to the outer surface. One set of side walls 34b parallel to each other have mutually opposed portions of the lower part of the liquid surface contact area AM shown by an alternate long and short dash line, which transmit the optical beam for analysis radiated from the light source 8 and are used as the photometric unit AL that optically measures the liquid sample.

In such an event, when a container is assumed, which has a cross-sectional shape in the horizontal direction same as the circumscribed quadrangle Qmin (see FIG. 26) of the minimum area that circumscribes the cross-sectional shape in the horizontal direction where the meniscus M is formed and at the same time, is made up with the same material as the wall portion Pw of the portion where the meniscus is formed, the wall portion Pw is configured in such a manner that the rising of the meniscus M which the liquid held in the reaction container 34 forms is lower than the rising of the meniscus formed by the liquid held in the assumed container. That is, one set of opening side wall 34c is configured in such a manner that the cross-sectional area in the horizontal direction is monotonously increased towards the opening 34d, and as shown in FIG. 17, the liquid surface contact area AM of the inner surface opens outwards to upwards by being adjacent to the parallel side walls 34b with the angle θ inclined, which becomes obtuse to the inner surface of the bottom wall 34a, and by inclining with respect to the vertical surface. Consequently, in the reaction container 34, the bottom wall 34a and opening side wall 34c inner surface become nearly parallel to the streamlines of sound flows Fcc and Fcw, and at the same time, the meniscus M of the liquid sample Ls which comes into contact with the opening side wall 34c becomes flat as compared to conventional reaction container whose side wall is vertical. In this event, the surface sound wave device 21 may be installed on the opening side wall 34c as shown by dotted line in FIG. 17.

In such an event, the reaction container 34 shall be of a protruded shape whose cross-section in the horizontal direction orthogonal to the depth direction of the recessed portion Pd in the liquid surface contact area AM where the meniscus is formed has an area smaller than the circumscribed rectangle Qmin shown in FIG. 26 and which contains all the segments that connect optional two points included in this horizontal cross section in this horizontal cross section so that the rising of the meniscus M which the liquid held forms becomes low. In other words, the recessed portion Pc has a space which the bottom wall 34a side portion occupies rather than the portion in which the meniscus M is formed becomes a protruded shape which contains all segments that connect optional two points inside the liquid holding unit PL in the liquid holding unit PL. Furthermore, for the reaction container 34, the projected image of the opening 34d to the horizontal surface is formed in such a manner as to contain all the optional horizontal cross-sections of the liquid holding unit PL so that the cross-sectional area in the horizontal direction does not greatly vary in the vertical direction. In other words, the projected image of the recessed portion Pd to the horizontal surface includes all the cross-sections in the horizontal direction of the recessed portion Pd on the bottom wall 34a side from the meniscus M.

Consequently, the liquid holding unit Pt becomes a protruded shape which contains all segments that connect optional two points inside the liquid holding unit PL in the liquid holding unit PL. Furthermore, the reaction container 34 has the opening side wall 34c configured in such a manner that at least the bottom wall 34a side from the portion where the meniscus M is formed monotonously decreases the cross sectional area of the liquid holding unit PL in the horizontal direction towards the bottom wall 34a.

Consequently, when the reaction container 34 causes the surface sound wave device 21 to be driven by the stirrer 20, the sound wave induced by the oscillator 21b propagates to the bottom wall 34a of the reaction container 34 through the inside of the piezoelectric substrate 21a and the acoustic matching layer 24, and as shown in FIG. 17, the sound wave Wa shown by an arrow leaks from the inner bottom surface of the bottom wall 34a to obliquely upward and into the liquid sample Ls which has close acoustic impedance.

As a result, in the liquid sample Ls, as shown in FIG. 17, counterclockwise sound flow Fcc and clockwise sound flow Fcw which reach the meniscus M are generated by the sound wave Wa, and sound flows Fcc and Fcw are predominant for the flow in the liquid sample Ls. In such an event, as shown in FIG. 17, in the liquid sample Ls, the meniscus M of the liquid sample Ls which comes into contact with the opening side wall 34c becomes close to flatness as shown by the solid line and sound flows Fcc and Fcw are likely to enter the portion where the liquid surface contact area AM comes into contact with the meniscus M. Also, the opening side wall 34c comes into contact with the adjacent bottom wall 34a at an obtuse angle θ as shown in FIG. 17. Consequently, the reaction container 34 is free of generation of any stagnant portion because the generated sound flows Fcc and Fcw are guided to the inner surface at the obtuse angle θ which the base wall 34a and opening side wall 34c make.

Consequently, as shown in FIG. 17, the automatic analyzer 1 using the reaction container 34 is able to uniformly stir the liquid sample Ls contactlessly over a wide range from the bottom unit to the meniscus M by the sound flows Fcc and Fcw. In addition, because the reaction container 34 is used housed in the storage chamber 6a installed to the reaction table 6, it can be disposed to the storage chamber that houses a cuvette of conventional automatic analyzer and can be used as it is.

Figure 18:
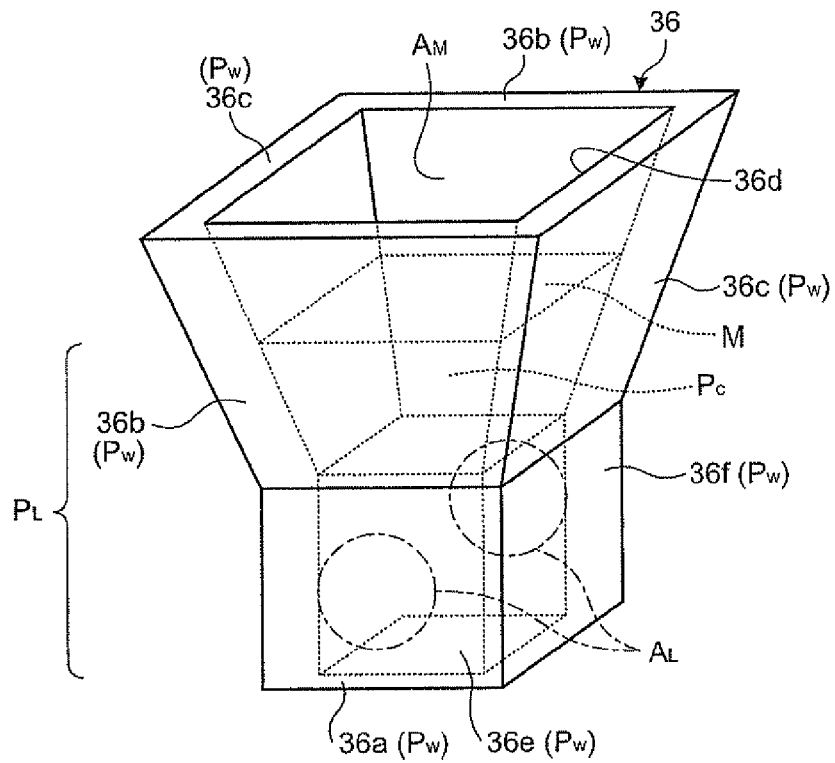
FIG. 18 is a perspective view of a modification of the reaction container related to the fourth embodiment.

In this event, the reaction container of the fourth embodiment may be the reaction container 36 shown in FIG. 18, if the liquid contact area has at least one set of opening side walls which open the liquid surface contact area outwards to upwards and is equipped with a surface sound wave device 21. The reaction container 36 is formed by the material same as that of reaction container 7, is equipped with a bottom wall 36a, one set of opening side wall 36b which opens to the outside, and one set of adjacent side walls 36c adjacent to the opening side wall 36b, and has an opening 36d for injecting a liquid at the top as the wall portion Pw.

Figure 19:
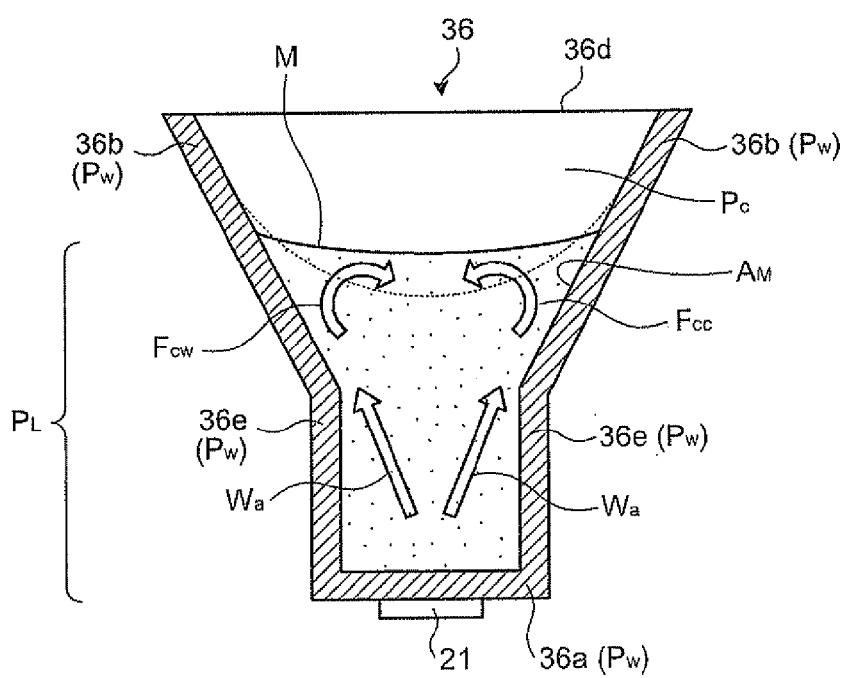
FIG. 19 is a longitudinal cross-sectional view of the reaction container shown in FIG. 18.

The bottom wall 36a has the surface sound wave device 21 mounted to the outer surface. One set of side walls 36b and one set of adjacent side walls 36c have the liquid contact area AM formed on the inner surface with which the meniscus M protruded downwards by a predetermined amount of liquid sample comes into contact, and has vertical walls 36e and 36f, which are parallel to each other at the lower part of the liquid surface contact area AM. One set of the opening side walls 36b and one set of adjacent side walls 36c have the liquid surface contact area AM on the inner surface open to the outside towards upwards by inclining with respect to the vertical surface. Consequently, in the reaction container 36, the meniscus M of the liquid sample Ls which comes into contact with the opening side wall 36b and adjacent side wall 36c becomes flat as compared to conventional reaction container whose side wall is vertical as shown in FIG. 19. On the other hand, the portion shown by the alternate short and long dash line of the vertical wall 36e transmits the optical beam for analysis radiated from the light source 8 and is used as the photometric unit AL that optically measures the liquid sample. The reaction container 36 forms the liquid holding unit PL by bottom wall 36a, one set of opening side walls 36b, one set of adjacent side walls 36c, and vertical walls 36e and 36f.

In such an event, the reaction container 36 shall be of a protruded shape whose cross-section in the horizontal direction orthogonal to the depth direction of the recessed portion Pd in the liquid surface contact area AM where the meniscus is formed has an area smaller than the circumscribed rectangle Qmin shown in FIG. 26 and which contains all the segments that connect optional two points included in this horizontal cross section in this horizontal cross section so that the rising of the meniscus M which the liquid held forms becomes low. Furthermore, for the reaction container 36, the projected image of the opening 36d to the horizontal surface is formed in such a manner as to contain all the optional horizontal cross-sections of the liquid holding unit PL so that the cross-sectional area in the horizontal direction does not greatly vary in the vertical direction. Consequently, the liquid holding unit PL becomes a protruded shape which contains all segments that connect optional two points inside the liquid holding unit PL in the liquid holding unit PL.

Consequently, when the reaction container 36 causes the surface sound wave device 21 to be driven by the stirrer 20, the sound wave induced by the oscillator 21b propagates to the bottom wall 36a of the reaction container 36 through the inside of the piezoelectric substrate 21a and the acoustic matching layer 24, and as shown in FIG. 19, the sound wave Wa shown by an arrow leaks from the inner bottom surface of the bottom wall 34a to obliquely upward and into the liquid sample Ls which has close acoustic impedance.

As a result, in the liquid sample Ls, as shown in FIG. 19, counterclockwise sound flow Fcc and clockwise sound flow Fcw which reach the meniscus M are generated by the sound wave Wa, and sound flows Fcc and Fcw are predominant for the flow in the liquid sample Ls. In such an event, as shown in FIG. 19, in the liquid sample Ls, the meniscus M of the liquid sample Ls which comes into contact with the opening side wall 34c becomes close to flatness as shown by the solid line and sound flows Fcc and Fcw are likely to enter the portion where the liquid surface contact area AM comes into contact with the meniscus M.

Consequently, as shown in FIG. 19, the automatic analyzer 1 using the reaction container 36 is able to uniformly stir the liquid sample Ls contactlessly over a wide range from the bottom unit to the meniscus M by the sound flows Fcc and Fcw. In addition, when the reaction container 36 has the outside shape designed to be housed in the storage chamber 6a installed to the reaction table 6, it can be used even in conventional automatic analyzer.

In this event, for reaction containers 34 and 36 of the fourth embodiment, the opening side walls 34c, 36b and adjacent side wall 36c were used as one set of side walls which open to the outside towards upwards, but these side walls 34c, 36b, and 36c may not be inclined walls but may be curved walls if they open to the outside towards upwards.

Figure 20:
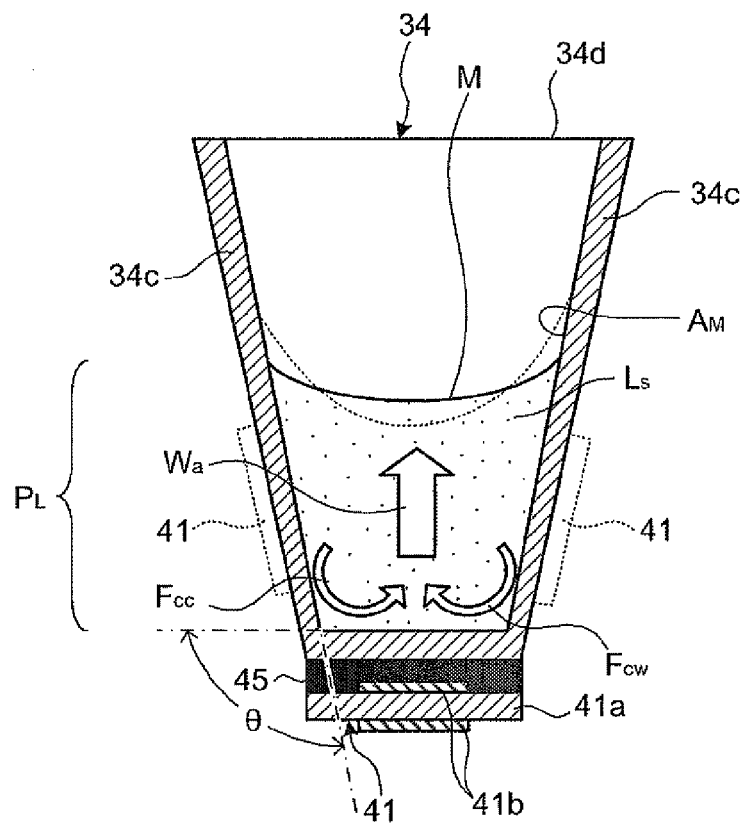
FIG. 20 is a cross-sectional view which shows a reaction container related to a fifth embodiment and which shows a stirrer that stirs a liquid held, together with the reaction container.
Figure 21:
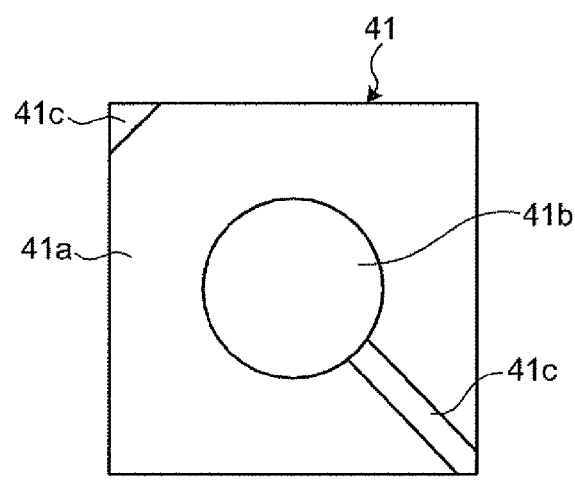
FIG. 21 is a bottom view of the sound wave generating unit of the stirrer of FIG. 20 as viewed from the bottom surface side.
Figure 22:
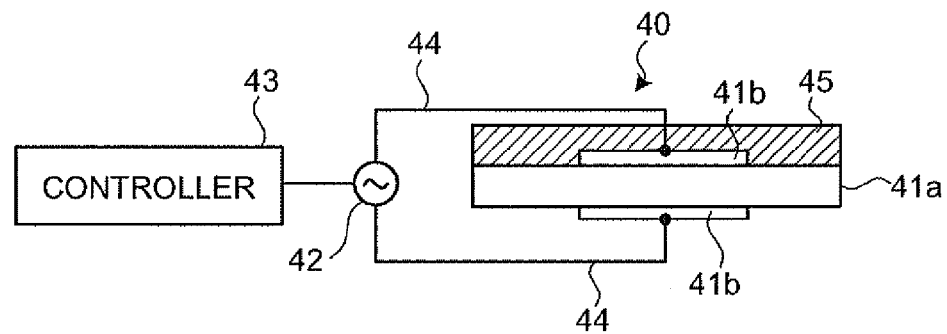
FIG. 22 is a schematic block diagram of the stirrer of FIG. 20.

Referring now to FIG. 20 to FIG. 22, the reaction container related to the fifth embodiment of the present invention will be described in detail. The reaction container of the first to the fourth embodiments used the surface sound wave device for a sound wave generating unit, whereas the reaction container of the fifth embodiment uses a thickness longitudinal oscillator for the sound wave generating unit for the reaction container of the fourth embodiment. FIG. 20 is a cross-sectional view that shows a stirrer using the thickness-longitudinal vibrator as a sound wave generating unit together with a reaction container.

In the reaction container 34, the liquid ample held to the liquid holding unit PL is stirred by the stirrer 40 mounted to the outer surface of the bottom wall 34a via the acoustic matching layer 45. The stirrer 40 includes a thickness-longitudinal vibrator 41, power supply 42, controller 43, and acoustic matching layer 45 as shown in FIG. 22.

The thickness-longitudinal vibrator 41 is a sound wave generating member that generates sound wave vertically to the plate surface, and as shown in FIG. 20, is mounted to the plane part outside of the bottom wall 34a. The thickness-longitudinal vibrator 41 has electrodes 41b mounted on both surfaces of a piezoelectric substrate 41a composed with piezoelectric zirconate titanate (PZT), and to each electrode 41b, an extraction electrode 41c (see FIG. 21) is connected. In such an event, the reaction container 34 has the thickness-longitudinal vibrator 41 mounted to the plane part (see the dotted line) outside of the opening side wall 34c. The power supply 42 is an AC power supply that drives the thickness-longitudinal vibrator 41 and applies high-frequency AC voltage of about several MHz to hundreds of MHz to the electrode 41b via wiring 44 shown in FIG. 22.

The controller 43 controls the power supply 42 and controls properties (frequency, intensity, phase, wave properties) of the sound wave which the thickness-longitudinal vibrator 41 generates, waveform (sinusoidal wave, triangular wave, rectangular wave, burst wave, etc.) or modulation (amplitude modulation and frequency modulation), etc. The acoustic matching layer 45 is a means to optimize the acoustic impedance between the reaction container 34 and the thickness-longitudinal vibrator 41, and gel, liquid, etc. can be used in addition to epoxy resin and other adhesives, shellac, and others. The acoustic matching layer 45 is adjusted to have the thickness of λ/4 with respect to the wavelength λ of the frequency which the thickness-longitudinal vibrator 41 generates in order to increase the sound wave transmission efficiency. Or the acoustic matching layer 45 shall be adjusted to be as thin as possible.

Consequently, the reaction container 34 has the retained liquid sample stirred as follows by the stirrer 40. First of all, the stirrer 40 drives the thickness-longitudinal vibrator 41 by the electric power supplied from the power supply 22 under the control by the controller 43. By this, the thickness-longitudinal vibrator 41 causes the electrode 41b shown in FIG. 20 to FIG. 22 to induce sound wave. The induced sound wave propagates to the bottom wall 34a of the reaction container 34 through the acoustic matching layer 45, and as shown in FIG. 20, the sound wave Wa shown by an arrow leaks from the inner surface of the bottom wall 34a to obliquely upward and into the liquid sample Ls which has close acoustic impedance.

As a result, in the liquid sample Ls, counterclockwise sound flow Fcc and clockwise sound flow Fcw which reach the meniscus M are generated by the sound wave Wa. In such an event, the reaction container 34 has the opening side wall 34c inclined at an angle θ, which becomes obtuse to the inner surface of the bottom wall 34a, and in the reaction container 34, the bottom wall 34a and opening side wall 34c inner surface become nearly parallel to the streamlines of sound flows Fcc and Fcw as shown in FIG. 20. Consequently, the reaction container 34 is free of generation of any stagnant portion because the generated sound flows Fcc and Fcw are guided to the inner surface at the obtuse angle which the base wall 34a and opening side wall 34c make. Also, as shown in FIG. 20, in the liquid sample Ls, the meniscus M of the liquid sample Ls which comes into contact with the opening side wall 34c becomes close to flatness as shown by the solid line and sound flows Fcc and Fcw are likely to enter the portion where the liquid surface contact area AM comes into contact with the meniscus M.

Consequently, as shown in FIG. 20, the automatic analyzer 1 using the reaction container 34 and the stirrer 40 is able to uniformly stir the liquid sample Ls contactlessly over a wide range from the bottom unit to the meniscus M by the sound flows Fcc and Fcw.

Figure 23:
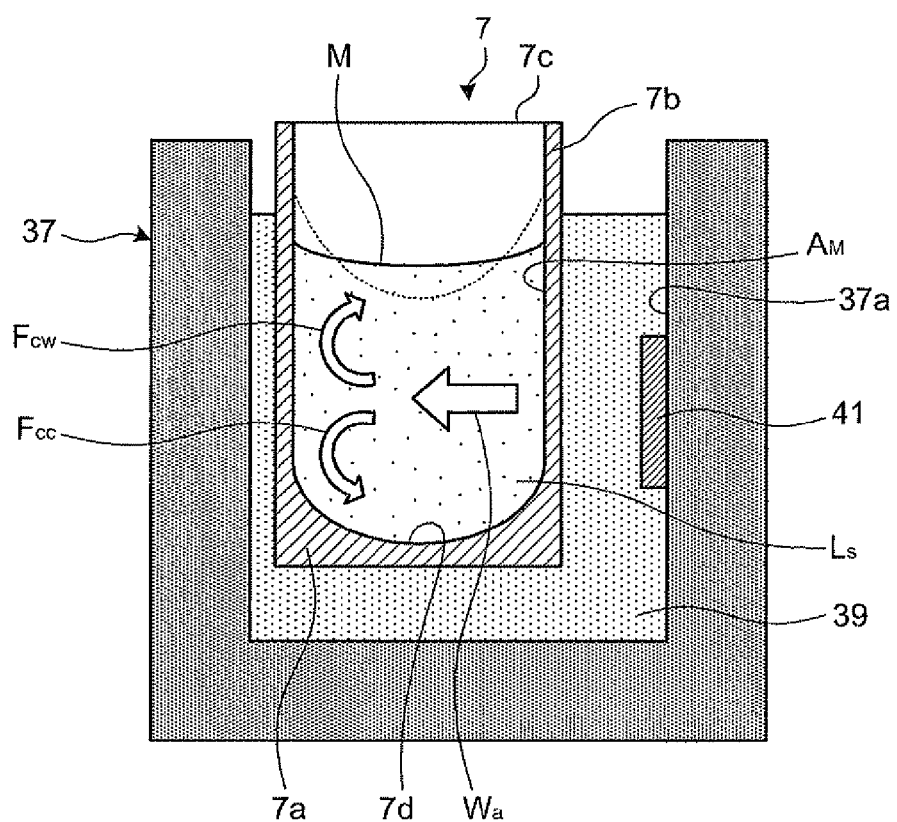
FIG. 23 is a cross-sectional view that shows a reaction container related to a sixth embodiment.
Figure 24:
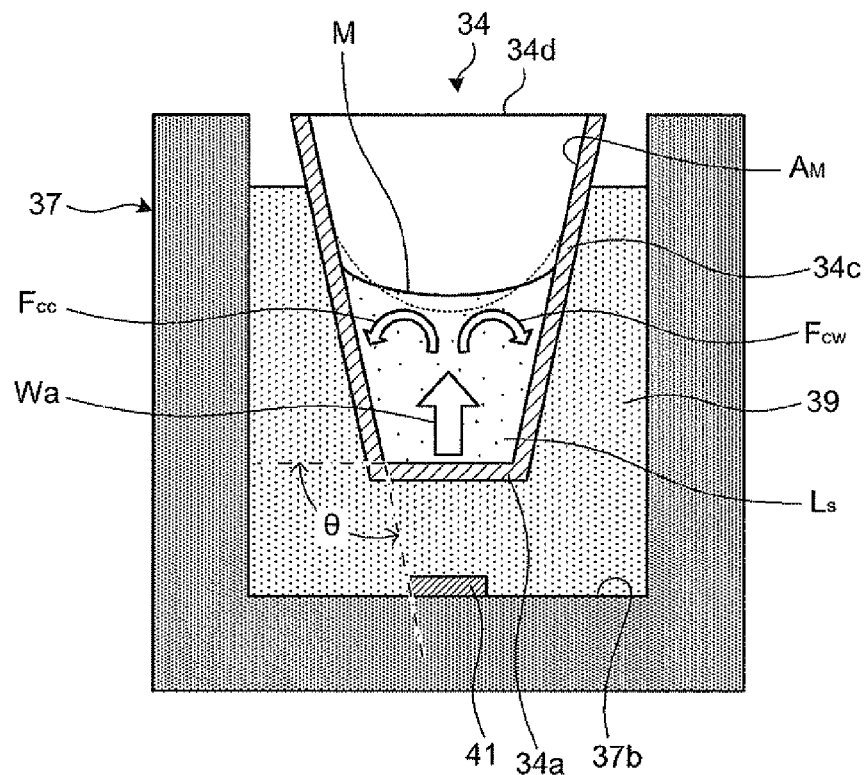
FIG. 24 is a cross-sectional view that shows another example of the reaction container related to the sixth embodiment.

Referring now to FIG. 23 and FIG. 24, a reaction container related to a sixth embodiment of the present invention will be described in detail. The reaction containers of the first to the fifth embodiments have a sound wave generating unit which stirs the liquid sample held installed in contact with the reaction containers, whereas the reaction container of the sixth embodiment has the sound generating unit installed at a remote place. FIG. 23 is a cross-sectional view that shows the reaction container related to the sixth embodiment. FIG. 24 is a cross-sectional view that shows another example of the reaction container related to the sixth embodiment.

For the reaction container of the sixth embodiment, the reaction container 7 of the first embodiment is used, and the reaction container 7 is housed in a holder 37. The holder 37 is housed in a storage chamber 6a installed to the reaction table 6 and on the inside wall 37a, the thickness-longitudinal vibrator 41 is installed. In addition, the holder 37 houses the reaction container 7 via a temperature-controlled liquid 39. Consequently, the reaction container 7 is installed at a remote location without making contact with the thickness-longitudinal vibrator 41.

Consequently, when in the reaction container 7 of the sixth embodiment, the thickness-longitudinal vibrator 41 is driven by the stirrer 40 under the control by the controller 43, sound wave induced by the thickness-longitudinal vibrator 41 propagates the temperature-controlled liquid 39 and impinges on the side wall 7b from the outer surface of the reaction container 7. The sound wave which impinges on the side wall 7b propagates the inside of the side wall 7b; then, as shown in FIG. 23, sound wave Wa shown by the arrow leaks in the horizontal direction into the liquid sample Ls close to the acoustic impedance from the side wall 7b.

As a result, for the reaction container 7, clockwise sound flow Fcw which reach the meniscus M and counterclockwise sound flow Fcc which flows along the curved surface of the inner bottom surface 7d are generated in the liquid sample Ls by the sound wave Wa. In such an event as shown in FIG. 23, the reaction container 7 has the inner surfaces of bottom wall 7a and the side wall 7b formed nearly parallel to the streamline of the sound flow Fcc generated in the liquid by sound wave. Consequently, the counterclockwise sound flow Fcc is guided by the inner bottom surface 7d and flows smoothly, and generation of the stagnant portion can be suppressed. Consequently, the reaction container 7 provides outstanding stirring efficiency, and in spite of contactlessness, the liquid sample Ls held is stirred uniformly in a short time.

Figure 10:
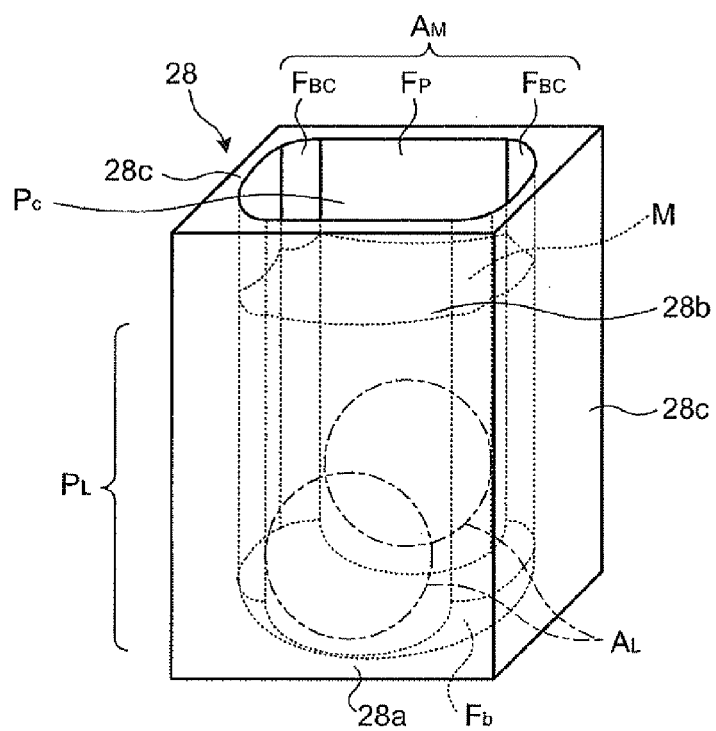
FIG. 10 is a perspective view that shows a fifth modification of the reaction container related to the first embodiment.

Furthermore, in such an event, as shown in FIG. 23, in the reaction container 7, the meniscus M of the liquid sample Ls becomes close to flatness as shown in the cases of FIG. 4, FIG. 10 and FIG. 12, etc. and sound flows Fcc and Fcw are likely to enter the portion where the liquid surface contact area AM comes into contact with the meniscus M. Consequently, the automatic analyzer 1 using the reaction container 7 and the stirrer 40 is able to uniformly stir the liquid sample Ls contactlessly over a wide range from the bottom unit to the meniscus M by the sound flows Fcc and Fcw.

In this way, because the reaction container of the sixth embodiment has the thickness-longitudinal vibrator 41 installed at the location distant from the reaction container 7, as shown in FIG. 24, the reaction container 34 (see FIG. 16 and FIG. 17) of the fourth embodiment can be used, too. In such an event, the holder 37 has the thickness-longitudinal vibrator 41 installed on the inner bottom wall 37b as shown in FIG. 24.

When the reaction container of the sixth embodiment is configured as shown in FIG. 24 and the thickness-longitudinal vibrator 41 is driven by the stirrer 40 under the control by the controller 43, the sound wave which is induced by the thickness-longitudinal vibrator 41 propagates the temperature-controlled liquid 39 and impinges on the bottom wall 34a from the outer surface of the reaction container 34. The sound wave incident to the bottom wall 34a propagates the inside of the bottom wall 34a; then, as shown in FIG. 24, sound wave Wa shown by the arrow leaks upwards into the liquid sample Ls close to the acoustic impedance from the bottom wall 34a.

As a result, in the reaction container 34, clockwise sound flow Fcw which reach the meniscus M and counterclockwise sound flow Fcc are generated in the liquid sample Ls by the sound wave Wa. In such an event, as shown in FIG. 24, the reaction container 34 has the opening side wall 34c inclined at an angle θ, which becomes obtuse to the inner surface of the bottom wall 34a, and in the reaction container 34, the bottom wall 34a and opening side wall 34c inner surface become nearly parallel to the streamlines of sound flows Fcc and Fcw. Consequently, the reaction container 34 is free of generation of any stagnant portion because the generated sound flows Fcc and Fcw are guided to the inner surface at the obtuse angle which the base wall 34a and opening side wall 34c make. Also, as shown in FIG. 24, in the liquid sample Ls, the meniscus M of the liquid sample Ls which comes into contact with the opening side wall 34c becomes close to flatness as shown by the solid line and sound flows Fcc and Fcw are likely to enter the portion where the liquid surface contact area AM comes into contact with the meniscus M.

Consequently, the automatic analyzer 1 using the reaction container 34 and the stirrer 40 is able to uniformly stir the liquid sample Ls contactlessly over a wide range from the bottom unit to the meniscus M by these sound flows Fcc and Fcw. In addition, because the holder 37 is able to be housed in the storage chamber 6a installed to the reaction table 6, the reaction containers 7 and 34 of the sixth embodiment can be used in conventional automatic analyzer, too.

Since the automatic analyzer 1 which uses reaction containers 7 and 34 of the sixth embodiment and the stirrer 40 has the thickness-longitudinal vibrator 41 installed at a location distant from the reaction containers 7 and 34, the automatic analyzer 1 provides an advantage of increased degree of freedom in terms of mechanical design of the stirrer 40 and the automatic analyzer 1.

For the first to the sixth embodiments, reaction containers were discussed as a stirring container, but if it is a container in which trace amount of the order of μL of a liquid held can be stirred, the container shall not be limited to a reaction container but may be used as reagent containers and other containers.

In addition, in the first to the sixth embodiments, reaction containers of the present invention were discussed by exemplifying containers whose horizontal cross section of the container outer shape (outer shape of the container wall portion) is a square or a rectangle, which is easy to manufacturer or arranged in a row. However, the reaction container of the present invention may have a cross section in the horizontal direction of the container outer shape not only of a quadrangle but also of a polygon with five or more corners (for example, hexagon). That is, there is no problem when the reaction container of the present invention may not be limited to a quadrangle (quadrangular prism) but may be suitably a hexagonal prism, or octangular prism, or other rectangular columns, as far as the container wall portions are configured in such a manner that generation of a stagnant portion is suppressed in the container inside.

When a conventional stirring container is miniaturized to have a capacity of several μL order, in particular, a stagnant portion is generated at the bottom corner portion of the container, and the portion can not be thoroughly stirred. However, according to the stirring container and the analyzer of the present invention discussed above, generation of a stagnant portion in the bottom corner portions of the container can be suppressed, and the liquid which the container holds can be uniformly stirred.

In addition, when a conventional stirring container is miniaturized to have a capacity of several μL order, in particular, the meniscus of the liquid held rises, and the rising meniscus portion cannot be thoroughly stirred. However, according to the stirring container and the analyzer of the present invention discussed above, the rising of the meniscus is able to be suppressed, and the liquid which the container holds can be uniformly stirred.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A stirring container in which liquid is contained, the stirring container being used in an analyzer for measuring a property of the liquid, the stirring container comprising:
a recessed portion in which the liquid is held so that a meniscus is formed at a surface of the liquid, the recessed portion being formed by a wall portion including opposing, outer side walls and a bottom wall, a cross section of the wall portion being configured for forming a meniscus between the opposing, outer side walls by the liquid held in the recessed portion at a position lower than a meniscus formed by the liquid held in an assumed container having a cross section in a direction orthogonal to a depth direction of the recessed portion equal to a cross section of a rectangle having a minimum area and circumscribing a portion of the opposing, outer side walls of the stirring container where the meniscus is formed in the relevant direction, the portion where the meniscus is formed in the assumed container being made of a same material as a part of the wall portion of the stirring container where the meniscus is formed; and
a sound wave generating unit disposed outside of the wall portion, the sound wave generating unit generating surface acoustic sound waves for stirring the liquid held in the recessed portion, wherein the sound wave generating unit and the walls are disposed at predetermined positions and angles with respect to each other such that when the sound wave generating unit generates the surface acoustic sound waves, the generated sound waves are capable of preventing stagnant portions of the liquid when the liquid is being stirred without relative movement between the sound wave generating unit and the walls, and without adjustment of frequency of the surface acoustic sound waves,
wherein the cross section of the stirring container in the direction orthogonal to the depth direction of the recessed portion, at the position where the meniscus is formed, is smaller in area than the circumscribing rectangle, and portions of the cross section of the recessed portion protrude inward relative to the cross section of the circumscribing rectangle;
wherein the stirring container further comprises a pair of side walls provided closer to the bottom wall than the portion where the meniscus is formed between the opposing, outer side walls, and which are parallel to each other; and a photometric unit which is provided on part of the pair of side walls and on which light of a predetermined wavelength impinges from a direction perpendicular to the pair of side walls in order to measure a property of the liquid held in the recessed portion, and
wherein the recessed portion comprises a first recessed portion and a second recessed portion under the first recessed portion, wherein adjacent perpendicular walls of the first recessed portion are joined by curved sections, and wherein adjacent perpendicular walls of the second recessed portion are not joined by curved sections.

2. The stirring container according to claim 1, wherein a wavelength in the liquid of a sound wave generated by the sound wave generating unit is substantially sufficiently short with respect to the rising of the meniscus formed by the liquid in the assumed container.

3. The stirring container according to claim 2, wherein $h \geqq 10 \cdot \lambda_L$ is satisfied where h is the rising of the meniscus, and $\lambda_L$ is a wavelength of the sound wave in the liquid.

4. The stirring container according to claim 1, wherein the depth direction is vertical, and the direction orthogonal to the depth direction is horizontal.

5. The stirring container according to claim 1, wherein the sound wave generating unit is a surface sound wave device which has a piezoelectric substrate and an interdigital transducer formed on the piezoelectric substrate.

6. The stirring container according to claim 1, wherein a surface outside of the wall portion on which the sound wave generated by the sound wave generating unit impinges is formed of flat surfaces.

7. The stirring container according to claim 6, wherein the sound wave generating unit is disposed to be in contact with an outside of the side wall or the bottom wall of the wall portion.

8. The stirring container according to claim 5, wherein a sound flow is predominant in a stream in the liquid generated by the surface sound wave device.

9. The stirring container according to claim 1, further comprising an opening for injecting the liquid held in the recessed portion, wherein a projected image of the opening in the depth direction of the recessed portion includes all cross sections in the direction orthogonal to the depth direction of the recessed portion from the meniscus to the bottom wall.

10. The stirring container according to claim 9, wherein a space occupied by a liquid holding portion which is the recessed portion closer to the bottom wall than a portion in contact with the meniscus, forms convexity that includes all segments that connect any two points included in the space.

11. The stirring container according to claim 9, wherein the wall portion has portions with different thicknesses so that an outer shape of the stirring container is a rectangular parallelepiped or a rectangular column.

12. The stirring container according to claim 9, wherein the side walls on an opening side from the portion where the meniscus is formed are configured so that cross sectional areas in the direction orthogonal to the depth direction monotonously increase towards the opening.

13. A stirring container in which liquid is contained, the stirring container being used in an analyzer for measuring a property of the liquid, the stirring container comprising:
  a recessed portion in which the liquid is held so that a meniscus is formed at a surface of the liquid, the recessed portion being formed by a wall portion including upper side walls and lower side walls, and a bottom wall, a cross section of the wall portion being configured for forming a meniscus by the liquid held in the recessed portion at a position lower than a meniscus formed by the liquid held in an assumed container having a cross section in a direction orthogonal to a depth direction of the recessed portion equal to a cross section of a rectangle having a minimum area and circumscribing a portion of the upper side walls of the stirring container where the meniscus is formed in the relevant direction, the portion where the meniscus is formed in the assumed container being made of a same material as a part of the wall portion of the stirring container where the meniscus is formed;
  a sound wave generating unit disposed outside of the wall portion, the sound wave generating unit generating surface acoustic sound waves for stirring the liquid held in the recessed portion,
  wherein the cross section of the stirring container in the direction orthogonal to the depth direction of the recessed portion, at the position where the meniscus is formed, is smaller in area than the circumscribing rectangle, and portions of the cross section of the recessed portion protrude inward relative to the cross section of the circumscribing rectangle;
  an opening for injecting the liquid held in the recessed portion, wherein a projected image of the opening in the depth direction of the recessed portion includes all cross sections in the direction orthogonal to the depth direction of the recessed portion from the meniscus to the bottom wall;
  wherein the side walls on an opening side from the portion where the meniscus is formed are configured so that cross sectional areas in the direction orthogonal to the depth direction monotonously increase towards the opening; and
  wherein the stirring container further comprises a pair of side walls provided closer to a bottom wall than a portion which is configured so that the cross sectional areas monotonously increase towards the opening, the side walls being parallel to each other; and
  a photometric unit which is provided on part of the pair of side walls and on which light of a predetermined wavelength impinges from a direction perpendicular to the pair of side walls in order to measure a property of the liquid held in the recessed portion.

14. A stirring container in which liquid is contained, the stirring container being used in an analyzer for measuring a property of the liquid, the stirring container comprising:
  a recessed portion in which the liquid is held so that a meniscus is formed at a surface of the liquid, the recessed portion being formed by a wall portion including upper side walls and lower side walls, and a bottom wall, a cross section of the wall portion being configured for forming a meniscus by the liquid held in the recessed portion at a position lower than a meniscus formed by the liquid held in an assumed container having a cross section in a direction orthogonal to a depth direction of the recessed portion equal to a cross section of a rectangle having a minimum area and circumscribing a portion of the upper side walls of the stirring container where the meniscus is formed in the relevant direction, the portion where the meniscus is formed in the assumed container being made of a same material as a part of the wall portion of the stirring container where the meniscus is formed;
  a sound wave generating unit disposed outside of the wall portion, the sound wave generating unit generating surface acoustic sound waves for stirring the liquid held in the recessed portion,
  wherein the cross section of the stirring container in the direction orthogonal to the depth direction of the recessed portion, at the position where the meniscus is formed, is smaller in area than the circumscribing rectangle, and portions of the cross section of the recessed portion protrude inward relative to the cross section of the circumscribing rectangle;

an opening for injecting the liquid held in the recessed portion, wherein a projected image of the opening in the depth direction of the recessed portion includes all cross sections in the direction orthogonal to the depth direction of the recessed portion from the meniscus to the bottom wall;

wherein the side walls on an opening side from the portion where the meniscus is formed are configured so that cross sectional areas in the direction orthogonal to the depth direction monotonously increase towards the opening; and wherein a cross section of the recessed portion orthogonal to the depth direction of the recessed portion in the part on which the photometric unit is provided is smaller than a cross section of the recessed portion in the relevant direction in the portion where the meniscus is formed.

15. The stirring container according to claim 1, wherein the sound wave generating unit is disposed apart from the photometric unit.

16. The stirring container according to claim 15, wherein the sound wave generating unit is disposed in a wall other than the pair of side walls on which the photometric unit is provided.

17. The stirring container according to claim 15, wherein the sound wave generating unit is disposed on the bottom wall.

18. The stirring container according to claim 1, wherein the side wall in contact with the meniscus of the liquid has a non-affinity for the liquid.

19. An analyzer, comprising:
an analyzing unit for measuring a property of a liquid sample by stirring; and
a stirring container for holding the liquid sample, the liquid sample containing an analyte and a reagent, the stirring container comprising:
a recessed portion in which the liquid sample is held so that a meniscus is formed at a surface of the liquid sample, the recessed portion being formed by a wall portion including opposing, outer side walls and a bottom wall, a cross section of the wall portion being configured for forming a meniscus between the opposing, outer side walls by the liquid held in the recessed portion at a position lower than a meniscus formed by the liquid held in an assumed container having a cross section in a direction orthogonal to a depth direction of the recessed portion equal to a cross section of a rectangle having a minimum area and circumscribing a portion of the opposing, outer side walls of the stirring container where the meniscus is formed in the relevant direction, the portion where the meniscus is formed in the assumed container being made of a same material as a part of the wall portion of the stirring container where the meniscus is formed; and
a sound wave generating unit disposed outside of the wall portion, the sound wave generating unit generating surface acoustic sound waves for stirring the liquid sample held in the recessed portion, wherein the sound wave generating unit and the walls are disposed at predetermined positions and angles with respect to each other such that when the sound wave generating unit generates the surface acoustic sound waves, the generated sound waves are capable of preventing stagnant portions of the liquid when the liquid is being stirred without relative movement between the sound wave generating unit and the walls, and without adjustment of frequency of the surface acoustic sound waves, wherein the cross section of the stirring container in the direction orthogonal to the depth direction of the recessed portion, at the position where the meniscus is formed, is smaller in area than the circumscribing rectangle, and portions of the cross section of the recessed portion protrude inward relative to the cross section of the circumscribing rectangle;

wherein the stirring container further comprises a pair of side walls provided closer to the bottom wall than the meniscus formed between the opposing, outer side walls, the pair of side walls being parallel to each other; and a photometric unit which is provided on part of the pair of side walls and on which light of a predetermined wavelength impinges from a direction perpendicular to the pair of side walls in order to measure a property of the liquid held in the recessed portion, and wherein the recessed portion comprises a first recessed portion and a second recessed portion under the first recessed portion, wherein adjacent perpendicular walls of the first recessed portion are joined by curved sections, and wherein adjacent perpendicular walls of the second recessed portion are not joined by curved sections.

20. A stirring container in which liquid is contained, the stirring container being used in an analyzer for measuring a property of the liquid, comprising:
a recessed portion in which the liquid is held so that a meniscus is formed at a surface of the liquid, the recessed portion being formed by a wall portion including opposing, outer side walls and a bottom wall; and
a sound wave generating unit disposed outside of the wall portion, the sound wave generating unit generating surface acoustic sound waves for stirring the liquid held in the recessed portion, wherein the sound wave generating unit and the walls are disposed at predetermined positions and angles with respect to each other such that when the sound wave generating unit generates the surface acoustic sound waves, the generated sound waves are capable of preventing stagnant portions of the liquid when the liquid is being stirred without relative movement between the sound wave generating unit and the walls, and without adjustment of frequency of the surface acoustic sound waves;

wherein the stirring container further comprises a pair of side walls provided closer to the bottom wall than the meniscus formed between the opposing, outer side walls, the pair of side walls being parallel to each other; and a photometric unit which is provided on part of the pair of side walls and on which light of a predetermined wavelength impinges from a direction perpendicular to the pair of side walls in order to measure a property of the liquid held in the recessed portion, and wherein the recessed portion comprises a first recessed portion and a second recessed portion under the first recessed portion, wherein adjacent perpendicular walls of the first recessed portion are joined by curved sections, and wherein adjacent perpendicular walls of the second recessed portion are not joined by curved sections.

21. The stirring container according to claim 20, wherein the sound wave generating unit is disposed in contact with a plane part of the outside of the wall portion.

22. The stirring container according to claim 21, wherein the sound wave generating unit is fixed to the plane part of the outside of the wall portion.

23. The stirring container according to claim 21, wherein the sound wave generating unit is disposed on a portion where a wall thickness of the wall portion corresponding to a portion provided with the sound waves generated by the sound wave generating unit becomes constant.

24. The stirring container according to claim 21, wherein the sound wave generating unit is provided on at least one of the side walls or the bottom wall of the wall portion.

25. The stirring container according to claim 20, wherein the sound wave generating unit is a surface sound wave device which has a piezoelectric substrate and interdigital transducer formed on the piezoelectric substrate.

26. The stirring container according to claim 20, wherein a projected image in a horizontal surface of the recessed portion includes all cross sections in a horizontal direction of the recessed portion from the meniscus to the bottom wall.

27. The stirring container according to claim 26, wherein a second set of side walls closer to the bottom wall than the portion where the meniscus is formed are configured so that the cross sectional areas in the horizontal direction monotonously decreases toward the bottom wall.

28. The stirring container according to claim 26, wherein a space occupied by the portion closer to the bottom wall than the portion where the meniscus is formed forms a convexity that includes all segments that connect any two points included in the space.

29. The stirring container according to claim 20, wherein the wall portion has an outer shape which is a quadrangle or rectangular column.

30. The stirring container according to claim 29, wherein the wall portion has portions with different thicknesses so that an outer shape of the stirring container is a rectangular parallelepiped or a rectangular column.

31. An analyzer, comprising:
an analyzing unit for analyzing a liquid sample containing an analyte and a reagent; and a stirring container comprising:
a recessed portion in which the liquid sample is held so that a meniscus is formed at a surface of the liquid sample, the recessed portion being formed by a wall portion including opposing, outer side walls and a bottom wall; and
a sound wave generating unit disposed outside of the wall portion, the sound wave generating unit generating the surface acoustic sound waves for stirring the liquid sample held in the recessed portion, wherein the sound wave generating unit and the walls are disposed at predetermined positions and angles with respect to each other such that when the sound wave generating unit generates the surface acoustic sound waves, the generated sound waves are capable of preventing stagnant portions of the liquid when the liquid is being stirred without relative movement between the sound wave generating unit and the walls, and without adjustment of frequency of the surface acoustic sound waves;
wherein the stirring container further comprises a pair of side walls are provided closer to the bottom wall than the meniscus formed between the opposing, outer side walls, the pair of side walls being parallel to each other; and a photometric unit which is provided on part of the pair of side walls and on which light of a predetermined wavelength impinges from a direction perpendicular to the pair of side walls in order to measure a property of the liquid held in the recessed portion, and
wherein the recessed portion comprises a first recessed portion and a second recessed portion under the first recessed portion, wherein adjacent perpendicular walls of the first recessed portion are joined by curved sections, and wherein adjacent perpendicular walls of the second recessed portion are not joined by curved sections.

32. The analyzer according to claim 31, wherein the liquid sample is analyzed by aligning a plurality of the stirring containers.

* * * * *